(12) United States Patent
Mintz et al.

(10) Patent No.: US 10,169,875 B2
(45) Date of Patent: ***Jan. 1, 2019

(54) NAVIGATION OF TUBULAR NETWORKS

(71) Applicant: Auris Health, Inc., Redwood City, CA (US)

(72) Inventors: David S. Mintz, Mountain View, CA (US); Atiyeh Ghoreyshi, Richmond, CA (US); Prasanth Jeevan, San Mateo, CA (US); Yiliang Xu, Cupertino, CA (US); Gehua Yang, Wexford, PA (US); Matthew Joseph Leotta, Clifton Park, NY (US); Charles V. Stewart, Clifton Park, NY (US)

(73) Assignee: Auris Health, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/669,258

(22) Filed: Aug. 4, 2017

(65) Prior Publication Data

US 2017/0365055 A1 Dec. 21, 2017

Related U.S. Application Data

(63) Continuation of application No. 15/268,238, filed on Sep. 16, 2016, now Pat. No. 9,727,963.

(Continued)

(51) Int. Cl.
*G06T 7/00* (2017.01)
*A61B 1/04* (2006.01)
(Continued)

(52) U.S. Cl.
CPC ............ *G06T 7/0012* (2013.01); *A61B 1/005* (2013.01); *A61B 1/00009* (2013.01);
(Continued)

(58) Field of Classification Search
CPC ................................................... G06T 7/0012
See application file for complete search history.

(56) References Cited

U.S. PATENT DOCUMENTS

| 5,273,025 A | 12/1993 | Sakiyam et al. |
| 5,526,812 A | 6/1996 | Dumoulin et al. |

(Continued)

FOREIGN PATENT DOCUMENTS

| EP | 3 025 630 | 6/2016 |
| WO | WO 09/097461 | 6/2007 |

OTHER PUBLICATIONS

PCT International Search Report and Written Opinion for PCT Application No. PCT/US2016/052257, dated Nov. 29, 2016, 13 pages.

(Continued)

*Primary Examiner* — James M Pontius
(74) *Attorney, Agent, or Firm* — Knobbe Martens Olson & Bear LLP

(57) ABSTRACT

Methods and apparatuses provide improved navigation through tubular networks such as lung airways by providing improved estimation of location and orientation information of a medical instrument (e.g., an endoscope) within the tubular network. Various input data such as image data, EM data, and robot data are used by different algorithms to estimate the state of the medical instrument, and the state information is used to locate a specific site within a tubular network and/or to determine navigation information for what positions/orientations the medical instrument should travel through to arrive at the specific site. Probability distributions together with confidence values are generated corresponding to different algorithms are used to determine the medical instrument's estimated state.

30 Claims, 29 Drawing Sheets

Related U.S. Application Data

(60) Provisional application No. 62/220,770, filed on Sep. 18, 2015.

(51) Int. Cl.

| | | |
|---|---|---|
| *A61B 6/03* | (2006.01) | |
| *A61B 1/267* | (2006.01) | |
| *A61B 1/00* | (2006.01) | |
| *A61B 1/005* | (2006.01) | |
| *G06T 15/20* | (2011.01) | |
| *G06T 7/149* | (2017.01) | |
| *G06T 17/00* | (2006.01) | |
| *A61B 5/06* | (2006.01) | |
| *A61B 34/20* | (2016.01) | |
| *G06T 7/73* | (2017.01) | |
| *G06T 7/246* | (2017.01) | |
| *G06T 7/32* | (2017.01) | |
| *A61B 34/30* | (2016.01) | |
| *A61B 17/00* | (2006.01) | |
| *A61B 90/00* | (2016.01) | |
| *A61B 90/30* | (2016.01) | |
| *A61B 34/00* | (2016.01) | |
| *A61B 34/10* | (2016.01) | |

(52) U.S. Cl.
CPC ........ *A61B 1/0016* (2013.01); *A61B 1/00147* (2013.01); *A61B 1/00149* (2013.01); *A61B 1/04* (2013.01); *A61B 1/2676* (2013.01); *A61B 5/061* (2013.01); *A61B 6/032* (2013.01); *A61B 34/20* (2016.02); *G06T 7/149* (2017.01); *G06T 7/248* (2017.01); *G06T 7/32* (2017.01); *G06T 7/73* (2017.01); *G06T 15/205* (2013.01); *G06T 17/00* (2013.01); *A61B 34/25* (2016.02); *A61B 90/30* (2016.02); *A61B 2017/00809* (2013.01); *A61B 2034/105* (2016.02); *A61B 2034/107* (2016.02); *A61B 2034/2048* (2016.02); *A61B 2034/2051* (2016.02); *A61B 2034/252* (2016.02); *A61B 2034/301* (2016.02); *A61B 2090/3614* (2016.02); *G06T 2207/10068* (2013.01); *G06T 2207/10081* (2013.01); *G06T 2207/30061* (2013.01); *G06T 2207/30196* (2013.01)

(56) References Cited

U.S. PATENT DOCUMENTS

| | | |
|---|---|---|
| 5,831,614 A | 11/1998 | Tognazzini et al. |
| 5,935,075 A | 8/1999 | Casscells |
| 6,038,467 A | 3/2000 | De Bliek et al. |
| 6,047,080 A | 4/2000 | Chen |
| 6,059,718 A | 5/2000 | Taniguchi et al. |
| 6,063,095 A | 5/2000 | Wang et al. |
| 6,167,292 A | 12/2000 | Badano |
| 6,203,493 B1 | 3/2001 | Ben-Haim |
| 6,246,898 B1 | 6/2001 | Vesely |
| 6,425,865 B1 | 7/2002 | Salcudean et al. |
| 6,466,198 B1 | 10/2002 | Feinstein |
| 6,665,554 B1 | 12/2003 | Charles |
| 6,690,964 B2 | 2/2004 | Beiger et al. |
| 7,180,976 B2 | 2/2007 | Wink |
| 7,386,339 B2 | 6/2008 | Strommer et al. |
| 7,756,563 B2 | 7/2010 | Higgins |
| 7,789,874 B2 | 9/2010 | Yu et al. |
| 7,972,298 B2 | 7/2011 | Wallace et al. |
| 8,146,874 B2 | 4/2012 | Yu |
| 8,190,238 B2 | 5/2012 | Moll et al. |
| 8,394,054 B2 | 3/2013 | Wallace et al. |
| 8,672,837 B2 | 3/2014 | Roelle et al. |
| 8,821,376 B2 | 9/2014 | Tolkowsky |
| 8,968,333 B2 | 3/2015 | Yu et al. |
| 9,014,851 B2 | 4/2015 | Wong et al. |
| 9,138,129 B2 | 9/2015 | Diolaiti |
| 9,186,046 B2 | 11/2015 | Ramamurthy et al. |
| 9,271,663 B2 | 3/2016 | Walker et al. |
| 9,289,578 B2 | 3/2016 | Walker et al. |
| 9,314,306 B2 | 4/2016 | Yu |
| 9,326,822 B2 | 5/2016 | Lewis et al. |
| 9,408,669 B2 | 8/2016 | Kokish et al. |
| 9,452,018 B2 | 9/2016 | Yu |
| 9,459,087 B2 * | 10/2016 | Dunbar ............... G01B 7/003 |
| 9,504,604 B2 | 11/2016 | Alvarez |
| 9,561,083 B2 | 2/2017 | Yu et al. |
| 9,566,201 B2 | 2/2017 | Yu |
| 9,622,827 B2 | 4/2017 | Yu et al. |
| 9,629,682 B2 | 4/2017 | Wallace et al. |
| 9,636,184 B2 | 5/2017 | Lee et al. |
| 9,710,921 B2 | 7/2017 | Wong et al. |
| 9,713,509 B2 | 7/2017 | Schuh et al. |
| 9,727,963 B2 * | 8/2017 | Mintz ............... A61B 1/00149 |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,818,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 10,016,900 B1 | 7/2018 | Meyer et al. |
| 10,022,192 B1 | 7/2018 | Ummalaneni |
| 2001/0039421 A1 | 11/2001 | Heilbrun |
| 2002/0077533 A1 | 6/2002 | Bieger et al. |
| 2002/0120188 A1 | 8/2002 | Brock et al. |
| 2003/0195664 A1 | 10/2003 | Nowlin et al. |
| 2006/0015096 A1 | 10/2003 | Nowlin et al. |
| 2004/0047044 A1 | 3/2004 | Dalton |
| 2004/0263535 A1 | 12/2004 | Birkenbach et al. |
| 2005/0027397 A1 | 2/2005 | Niemeyer |
| 2005/0060006 A1 | 3/2005 | Pflueger |
| 2005/0085714 A1 | 4/2005 | Foley et al. |
| 2005/0143649 A1 | 6/2005 | Minai et al. |
| 2005/0193451 A1 | 9/2005 | Quistgaard et al. |
| 2005/0222554 A1 | 10/2005 | Wallace et al. |
| 2006/0004286 A1 | 1/2006 | Chang |
| 2006/0058643 A1 | 3/2006 | Florent |
| 2006/0098851 A1 | 5/2006 | Shoham |
| 2006/0173290 A1 | 8/2006 | Lavallee et al. |
| 2006/0184016 A1 | 8/2006 | Glossop |
| 2006/0258938 A1 | 11/2006 | Hoffman et al. |
| 2007/0055128 A1 | 3/2007 | Glossop |
| 2007/0123748 A1 | 5/2007 | Meglan |
| 2007/0135886 A1 | 6/2007 | Maschke |
| 2007/0208252 A1 | 9/2007 | Makower |
| 2007/0253599 A1 | 11/2007 | White et al. |
| 2008/0071140 A1 | 3/2008 | Gattani |
| 2008/0118118 A1 | 5/2008 | Berger |
| 2008/0161681 A1 | 7/2008 | Hauck |
| 2008/0183068 A1 | 7/2008 | Carls et al. |
| 2008/0183188 A1 | 7/2008 | Carls et al. |
| 2008/0201016 A1 | 8/2008 | Finlay |
| 2008/0212082 A1 | 9/2008 | Froggatt et al. |
| 2008/0218770 A1 | 9/2008 | Moll et al. |
| 2008/0243142 A1 | 10/2008 | Gildenberg |
| 2008/0245946 A1 | 10/2008 | Yu |
| 2008/0306490 A1 | 12/2008 | Lakin et al. |
| 2008/0312501 A1 | 12/2008 | Hasegawa et al. |
| 2009/0076476 A1 | 3/2009 | Barbagli et al. |
| 2009/0248036 A1 | 10/2009 | Hoffman et al. |
| 2009/0259230 A1 | 10/2009 | Khadem |
| 2009/0262109 A1 | 10/2009 | Markowitz et al. |
| 2009/0295797 A1 | 12/2009 | Sakaguchi |
| 2010/0039506 A1 | 2/2010 | Sarvestani et al. |
| 2010/0054536 A1 | 3/2010 | Huang |
| 2010/0161022 A1 | 6/2010 | Tolkowsky |
| 2010/0161129 A1 | 6/2010 | Costa et al. |

(56) References Cited

U.S. PATENT DOCUMENTS

| | | |
|---|---|---|
| 2010/0225209 A1 | 9/2010 | Goldberg |
| 2010/0240989 A1 | 9/2010 | Stoianovici |
| 2010/0292565 A1 | 11/2010 | Meyer |
| 2010/0298641 A1 | 11/2010 | Tanaka |
| 2010/0328455 A1 | 12/2010 | Nam et al. |
| 2011/0054303 A1 | 3/2011 | Barrick |
| 2010/0113852 A1 | 5/2011 | Prisco |
| 2011/0238082 A1 | 9/2011 | Wenderow |
| 2011/0248987 A1 | 10/2011 | Mitchell |
| 2011/0319714 A1 | 12/2011 | Roelle et al. |
| 2012/0056986 A1 | 3/2012 | Popovic |
| 2012/0065481 A1 | 3/2012 | Hunter |
| 2012/0069167 A1 | 3/2012 | Liu et al. |
| 2012/0082351 A1 | 4/2012 | Higgins |
| 2012/0209069 A1 | 8/2012 | Popovic |
| 2012/0219185 A1* | 8/2012 | Hu .................. G06K 9/32 382/103 |
| 2012/0241576 A1 | 9/2012 | Yu |
| 2013/0060146 A1 | 3/2013 | Yang et al. |
| 2013/0243153 A1 | 9/2013 | Sra |
| 2013/0246334 A1 | 9/2013 | Ahuja |
| 2013/0259315 A1 | 10/2013 | Angot et al. |
| 2013/0269109 A1 | 10/2013 | Yu |
| 2013/0345718 A1 | 12/2013 | Crawford |
| 2014/0094648 A1 | 4/2014 | Eno et al. |
| 2014/0114180 A1 | 4/2014 | Jain |
| 2014/0142591 A1 | 5/2014 | Alvarez et al. |
| 2014/0243849 A1* | 8/2014 | Saglam ............ A61B 19/2203 606/130 |
| 2014/0257746 A1 | 9/2014 | Dunbar et al. |
| 2014/0275988 A1 | 9/2014 | Walker et al. |
| 2014/0276033 A1 | 9/2014 | Brannan |
| 2014/0276391 A1 | 9/2014 | Yu |
| 2014/0276647 A1 | 9/2014 | Yu |
| 2014/0276935 A1 | 9/2014 | Yu |
| 2014/0276937 A1 | 9/2014 | Wong et al. |
| 2014/0277333 A1 | 9/2014 | Lewis et al. |
| 2014/0277334 A1 | 9/2014 | Yu et al. |
| 2014/0309527 A1 | 10/2014 | Namati et al. |
| 2014/0309649 A1 | 10/2014 | Alvarez et al. |
| 2014/0357953 A1 | 12/2014 | Roelle et al. |
| 2014/0364870 A1 | 12/2014 | Alvarez et al. |
| 2015/0025539 A1 | 1/2015 | Alvarez et al. |
| 2015/0051482 A1 | 2/2015 | Liu et al. |
| 2015/0054929 A1 | 2/2015 | Ito et al. |
| 2015/0066053 A1 | 3/2015 | Itkowitz et al. |
| 2015/0119637 A1* | 4/2015 | Alvarez ............ A61M 25/0009 600/102 |
| 2015/0223725 A1 | 8/2015 | Engel |
| 2015/0223902 A1 | 8/2015 | Walker et al. |
| 2015/0265368 A1* | 9/2015 | Chopra ............ A61B 5/062 600/424 |
| 2015/0287192 A1 | 10/2015 | Sasaki |
| 2015/0297864 A1 | 10/2015 | Kokish et al. |
| 2015/0374641 A1 | 12/2015 | Kim et al. |
| 2016/0100896 A1 | 4/2016 | Yu |
| 2016/0184032 A1 | 6/2016 | Romo et al. |
| 2016/0213432 A1 | 7/2016 | Flexman |
| 2016/0228032 A1 | 8/2016 | Walker et al. |
| 2016/0235946 A1 | 8/2016 | Lewis et al. |
| 2016/0338785 A1 | 11/2016 | Kokish et al. |
| 2016/0354582 A1 | 12/2016 | Yu et al. |
| 2016/0374541 A1 | 12/2016 | Agrawal et al. |
| 2017/0007343 A1 | 1/2017 | Yu |
| 2017/0065363 A1 | 3/2017 | Schuh et al. |
| 2017/0065364 A1 | 3/2017 | Schuh et al. |
| 2017/0079725 A1* | 3/2017 | Hoffman ............ A61B 1/00193 |
| 2017/0079726 A1* | 3/2017 | Hoffman ............ A61B 1/00193 |
| 2017/0084027 A1 | 3/2017 | Mintz et al. |
| 2017/0100199 A1 | 4/2017 | Yu et al. |
| 2017/0105804 A1 | 4/2017 | Yu |
| 2017/0119413 A1 | 5/2017 | Romo |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0290631 A1 | 10/2017 | Lee et al. |
| 2017/0333679 A1 | 11/2017 | Jiang |
| 2017/0340396 A1 | 11/2017 | Romo et al. |
| 2017/0360418 A1 | 12/2017 | Wong et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0184988 A1 | 7/2018 | Walker et al. |

OTHER PUBLICATIONS

Ciuti et al., 2012, Intra-operative monocular 30 reconstruction for image-guided navigation in active locomotion capsule endoscopy. Biomedical Robotics and Biomechatronics (Biorob), 4th IEEE Ras & Embs International Conference On IEEE.
Fallavollita et al., 2010, Acquiring multiview C-arm images to assist cardiac ablation procedures, EURASIP Journal on Image and Video Processing, vol. 2010, Article ID 871408, pp. 1-10.
Kumar et al., 2014, Stereoscopic visualization of laparoscope image using depth information from 3D model, Computer methods and programs in biomedicine 113(3):862-868.
Livatino et al., 2015, Stereoscopic visualization and 3-D technologies in medical endoscopic teleoperation, IEEE.
Luo et al., 2010, Modified hybrid bronchoscope tracking based on sequential monte carlo sampler: Dynamic phantom validation, Asian Conference on Computer Vision. Springer, Berlin, Heidelberg.
Mourgues et al., 2002, Flexible calibration of actuated stereoscopic endoscope for overlay inrobot assisted surgery, International Conference on Medical Image Computing and Computer-Assisted Intervention. Springer, Berlin, Heidelberg.
Nadeem et al., 2016, Depth Reconstruction and Computer-Aided Polyp Detection in Optical Colonoscopy Video Frames, arXiv preprint arXiv:1609.01329.
Point Cloud, Sep. 10, 2010, Wikipedia, 2 pp.
Racadio et al., Dec. 2007, Live 3D guidance in the interventional radiology suite, AJR, 189:W357-W364.
Sato et al., 2016, Techniques of stapler-based navigational thoracoscopic segmentectomy using virtual assisted lung mapping (VAL-MAP), Journal of Thoracic Disease, 8(Suppl 9):5716.
Shen et al., 2015, Robust camera localisation with depth reconstruction for bronchoscopic navigation. International Journal of Computer Assisted Radiology and Surgery, 10(6):801-813.
Solheim et al., May 14, 2009, Navigated resection of giant intracranial meningiomas based on intraoperative 3D ultrasound, Acta Neurochir, 151:1143-1151.
Song et al., 2012, Autonomous and stable tracking of endoscope instrument tools with monocular camera, Advanced Intelligent Mechatronics (AIM), 2012 IEEE-ASME International Conference on. IEEE.
Verdaasdonk et al., Jan. 23, 2012, Effect of microsecond pulse length and tip shape on explosive bubble formation of 2.78 µm Er,Cr;YSGG and 2.94 µm Er:YAG laser, Proceedings of SPIE, vol. 8221, 12.
Yip et al., 2012, Tissue tracking and registration for image-guided surgery, IEEE transactions on medical imaging 31(11):2169-2182.
Zhou et al., 2010, Synthesis of stereoscopic views from monocular endoscopic videos, Computer Vision and Pattern Recognition Workshops (CVPRW), 2010 IEEE Computer Society Conference on IEEE.

* cited by examiner

NAVIGATION OF TUBULAR NETWORKS

CROSS-REFERENCE TO RELATED APPLICATIONS

This application is a continuation of U.S. patent application Ser. No. 15/268,238, filed on Sep. 16, 2016, which claims the benefit of and priority to U.S. Provisional Application No. 62/220,770 filed Sep. 18, 2015, entitled "NAVIGATION OF TUBULAR NETWORKS", the entire disclosure of each of which is incorporated herein by reference.

BACKGROUND

1. Field of Art

This description generally relates to surgical robotics, and particularly to navigation of a medical instrument within a tubular network of a patient's body.

2. Description of the Related Art

Bronchoscopy is a medical procedure that allows a physician to examine the inside conditions of a patient's lung airways, such as bronchi and bronchioles. The lung airways carry air from the trachea, or windpipe, to the lungs. During the medical procedure, a thin, flexible tubular tool, known as a bronchoscope, may be inserted into the patient's mouth and passed down the patient's throat into his/her lung airways, and patients are generally anesthetized in order to relax their throats and lung cavities for surgical examinations and operations during the medical procedure.

A conventional bronchoscope typically includes a light source and a small camera that allows a physician to inspect a patient's windpipe and airways, and a rigid tube may be used in conjunction with the bronchoscope for surgical purposes, e.g., when there is a significant amount of bleeding in the lungs of the patient or when a large object obstructs the throat of the patient. When the rigid tube is used, the patient is often anesthetized. Coincident with the rise of other advanced medical devices, the use of robotic bronchoscopes are increasingly becoming a reality. Robotic bronchoscopes provide tremendous advantages in navigation through tubular networks. They are easy to use and allow therapy and biopsies to be administered conveniently even during the bronchoscopy stage.

Apart from mechanical devices or platforms, e.g., robotic bronchoscopes described above, various methods and software models may be used to help with the surgical operations. As an example, a computerized tomography (CT) scan of the patient's lungs is often performed during pre-operation of a surgical examination. Data from the CT scan may be used to generate a three dimensional (3D) model of airways of the patient's lungs, and the generated 3D model enables a physician to access a visual reference that may be useful during the operative procedure of the surgical examination.

However, previous techniques for navigation of tubular networks still have challenges, even when employing medical devices (e.g., robotic bronchoscopes) and when using existing methods (e.g., performing CT scans and generating 3D models). As one example, motion estimation of a medical device (e.g., a bronchoscope tool) inside a patient's body may not be accurate based on location and orientation change of the device, and as a result the device's position may not be accurately or correctly localized inside the patient's body in real time. Inaccurate location information for such an instrument may provide misleading information to the physician that uses the 3D model as a visual reference during medical operation procedures.

Thus, there is a need for improved techniques for navigating through a network of tubular structures.

SUMMARY

The methods and apparatus disclosed herein provide improved navigation through tubular networks such as lung airways by providing improved estimation of location and orientation information of a medical instrument like a flexible or rigid elongated medical instrument (e.g., an endoscope) within the tubular network.

As one example, the apparatus is a robotic endoscopic tool to acquire "raw" location and orientation information (collectively, input data) of a desired anatomical site or of the endoscopic tool within the tubular network. The endoscopic tool includes a flexible tip and an instrument device manipulator (IDM) coupled to the endoscopic tool. Devices such as an electromagnetic sensor (EM sensor), an imaging device (e.g., optical sensor), and a robotic control system controlling the medical instrument are coupled to the instrument tip to collect the input data as the endoscopic tool enters and navigates through the tubular network. The IDM is used to control movement and position of different robotic components (e.g., the endoscopic tool) of the surgical robotic system. A processor is coupled to the endoscopic tool to receive the input data to determine moment-by-moment movements and location and orientation information of the medical instrument (e.g., a instrument tip) within the tubular network.

The processor is instructed by a navigation configuration system to use the input data to estimate the state of the medical instrument, which may include information such as position, orientation, relative and absolute depth, branch selection, etc. The processor may be further instructed to use the estimated state to locate a specific site within a tubular network and/or to determine navigation information for what positions/orientations the medical instrument should travel through to arrive at the specific site, which may be referred to as the output data or navigation data.

The navigation configuration system further includes multiple algorithm modules employing various navigation algorithms for providing the estimated state and navigation data. Example algorithms used include EM-based algorithms, image-based algorithms, and robot-based algorithms. The estimated state and navigation data generated after employing these various algorithms makes use of any one or more of the EM-based input data, image-based input data, and robot-based input data.

In some embodiments, probability distributions together with confidence values are generated by the algorithm modules, which are used to determine the medical instrument's estimated state. The "probability" of the "probability distribution", as used herein, refers to a likelihood of an estimation or identification of location and/or orientation of the medical instrument being correct. For example, different probabilities may be calculated indicating the relative likelihood that the medical instrument is in one of several different possible airways within the lung. In contrast, the "confidence value, as used herein, reflects a measure of confidence in the estimation of the state provided by one of the algorithms. For example, relatively close to the airway opening, a particular algorithm may have a high confidence in its estimations of medical instrument position and orientation; but further into the bottom of the lung the medical instrument travels, that confidence value may drop. Generally, the confidence value is based on one or more "external" factors relating to the process by which a result is determined, whereas probability is a relative measure that arises when trying to determine possible results from a single algorithm. The algorithms, probabilities, and confidence values may be variously combined to arrive at the estimated state and navigation data.

In one embodiment, before executing an actual surgical operation on a patient, a sequence of pre-operative steps employing the improved navigation of surgical instruments (e.g., endoscopic) within a tubular network of the patient may be taken. Initially, a CT scan of the tubular network is obtained to generate a 3D model of the tubular network. A target area (e.g., a lesion to biopsy) within the tubular network is selected and a corresponding path for a surgical instrument to travel through the tubular network to reach the target area is automatically planned and displayed to a user (e.g., a physician responsible for the surgical operation). After the path is determined, a virtual endoscopic may be applied to travel through the tubular network to arrive at the target area. In the actual surgical operation, the CT scan, the generated 3D model as well as other input data (e.g., image data, EM data, robot data collected over the duration of the surgery) is combined and repeatedly analyzed during the surgery via the surgical configuration system to provide an estimation of the real-time movement information and location/orientation information of the surgical instrument (e.g., the endoscope) within the tubular network along with navigation information, which allows for more convenient operations by the physician.

Reference will now be made in detail to several embodiments, examples of which are illustrated in the accompanying figures. It is noted that wherever practicable similar or like reference numbers may be used in the figures and may indicate similar or like functionality. The figures depict embodiments of the described system (or method) for purposes of illustration only. One skilled in the art will readily recognize from the following description that alternative embodiments of the structures and methods illustrated herein may be employed without departing from the principles described herein.

DETAILED DESCRIPTION OF DRAWINGS

I. Surgical Robotic System

Figure 1A:
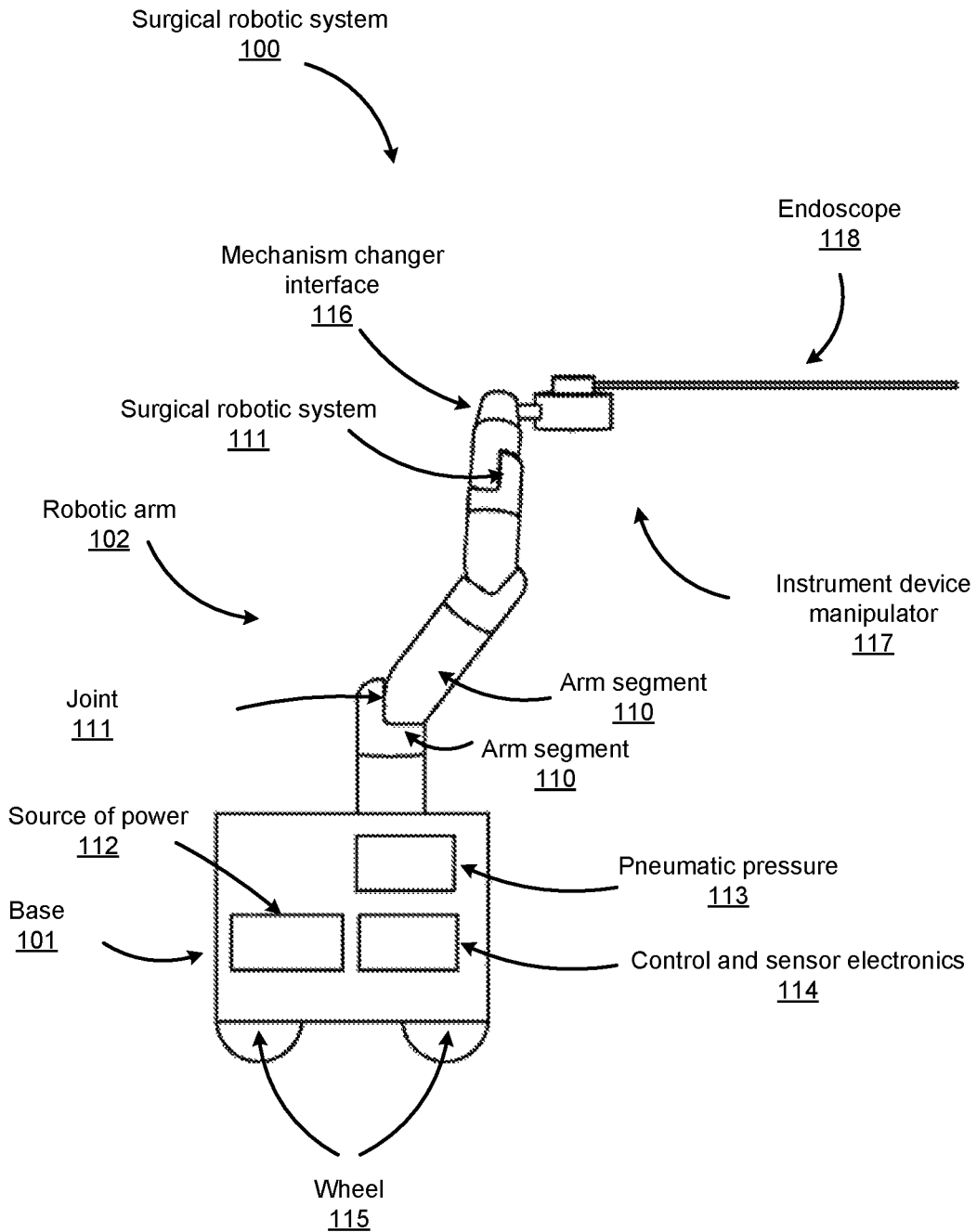
FIG. 1A (FIG. 1A) shows an example surgical robotic system, according to one embodiment.

FIG. 1A shows an example surgical robotic system 100, according to one embodiment. The surgical robotic system 100 includes a base 101 coupled to one or more robotic arms, e.g., robotic arm 102. The base 101 is communicatively coupled to a command console, which is further described with reference to FIG. 2 in Section II. COMMAND CONSOLE. The base 101 can be positioned such that the robotic arm 102 has access to perform a surgical procedure on a patient, while a user such as a physician may control the surgical robotic system 100 from the comfort of the command console. In some embodiments, the base 101 may be coupled to a surgical operating table or bed for supporting the patient. Though not shown in FIG. 1 for purposes of clarity, the base 101 may include subsystems such as control electronics, pneumatics, power sources, optical sources, and the like. The robotic arm 102 includes multiple arm segments 110 coupled at joints 111, which provides the robotic arm 102 multiple degrees of freedom, e.g., seven degrees of freedom corresponding to seven arm segments. The base 101 may contain a source of power 112, pneumatic pressure 113, and control and sensor electronics 114—including components such as a central processing unit, data bus, control circuitry, and memory—and related actuators such as motors to move the robotic arm 102. The electronics 114 in the base 101 may also process and transmit control signals communicated from the command console.

In some embodiments, the base 101 includes wheels 115 to transport the surgical robotic system 100. Mobility of the surgical robotic system 100 helps accommodate space constraints in a surgical operating room as well as facilitate appropriate positioning and movement of surgical equipment. Further, the mobility allows the robotic arms 102 to be configured such that the robotic arms 102 do not interfere with the patient, physician, anesthesiologist, or any other equipment. During procedures, a user may control the robotic arms 102 using control devices such as the command console.

In some embodiments, the robotic arm 102 includes set up joints that use a combination of brakes and counter-balances to maintain a position of the robotic arm 102. The counter-balances may include gas springs or coil springs. The brakes, e.g., fail safe brakes, may be include mechanical and/or electrical components. Further, the robotic arms 102 may be gravity-assisted passive support type robotic arms.

Each robotic arm 102 may be coupled to an instrument device manipulator (IDM) 117 using a mechanism changer interface (MCI) 116. The IDM 117 can be removed and replaced with a different type of IDM, for example, a first type of IDM manipulates an endoscope, while a second type of IDM manipulates a laparoscope. The MCI 116 includes connectors to transfer pneumatic pressure, electrical power, electrical signals, and optical signals from the robotic arm 102 to the IDM 117. The MCI 116 can be a set screw or base plate connector. The IDM 117 manipulates surgical instruments such as the endoscope 118 using techniques including direct drive, harmonic drive, geared drives, belts and pulleys, magnetic drives, and the like. The MCI 116 is interchangeable based on the type of IDM 117 and can be customized for a certain type of surgical procedure. The robotic 102 arm can include a joint level torque sensing and a wrist at a distal end, such as the KUKA AG® LBR5 robotic arm.

The endoscope 118 is a tubular and flexible surgical instrument that is inserted into the anatomy of a patient to capture images of the anatomy (e.g., body tissue). In particular, the endoscope 118 includes one or more imaging devices (e.g., cameras or other types of optical sensors) that capture the images. The imaging devices may include one or more optical components such as an optical fiber, fiber array, or lens. The optical components move along with the tip of the endoscope 118 such that movement of the tip of the endoscope 118 results in changes to the images captured by the imaging devices. The endoscope 118 is further described with reference to FIGS. 3A-4B in Section IV. Endoscope.

Robotic arms 102 of the surgical robotic system 100 manipulate the endoscope 118 using elongate movement members. The elongate movement members may include pull wires, also referred to as pull or push wires, cables, fibers, or flexible shafts. For example, the robotic arms 102 actuate multiple pull wires coupled to the endoscope 118 to deflect the tip of the endoscope 118. The pull wires may include both metallic and non-metallic materials such as stainless steel, Kevlar, tungsten, carbon fiber, and the like. The endoscope 118 may exhibit nonlinear behavior in response to forces applied by the elongate movement members. The nonlinear behavior may be based on stiffness and compressibility of the endoscope 118, as well as variability in slack or stiffness between different elongate movement members.

Figure 1B:
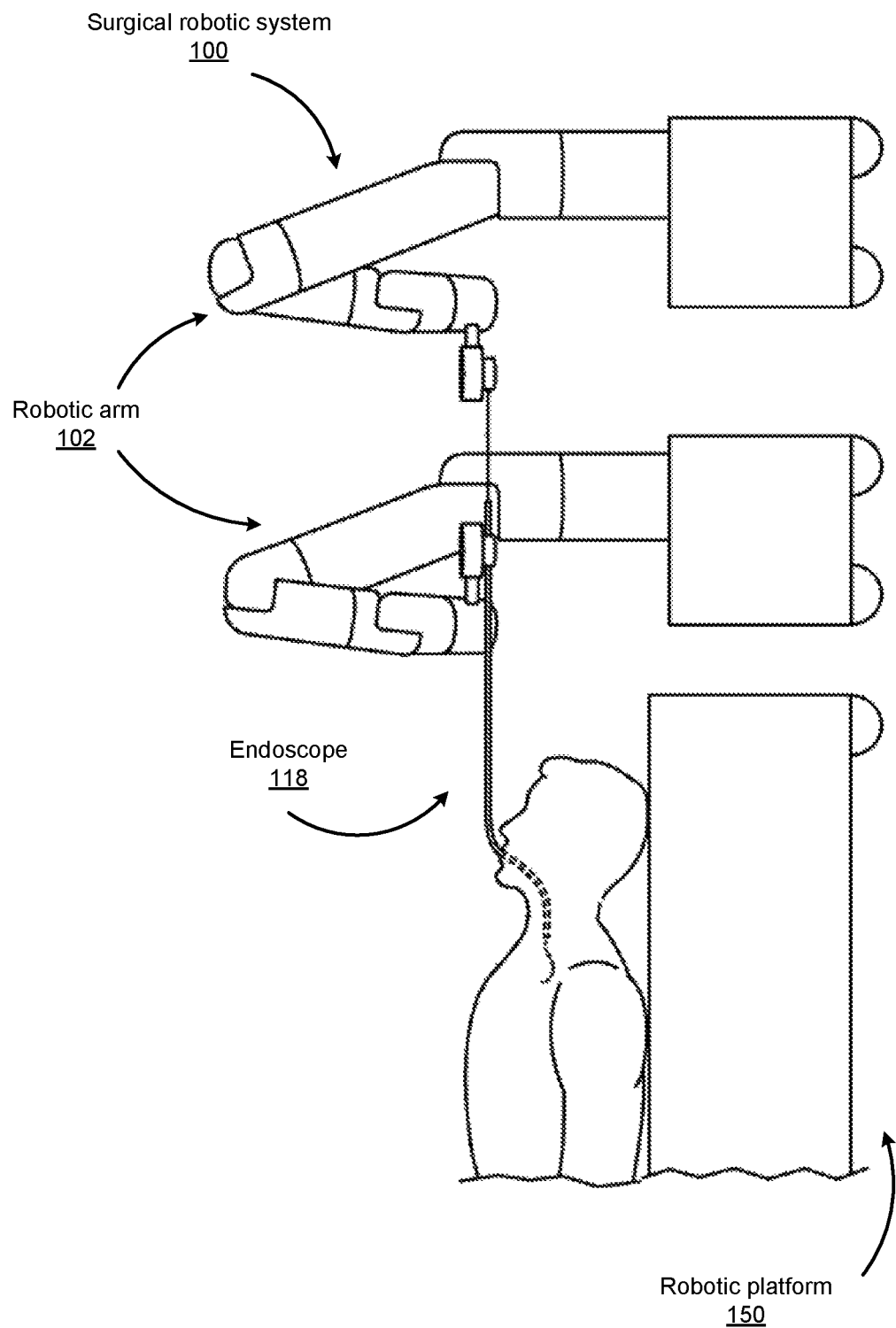
FIGS. 1B-1F show various perspective views of a robotic platform coupled to the surgical robotic system shown in FIG. 1A, according to one embodiment.
Figure 1C:
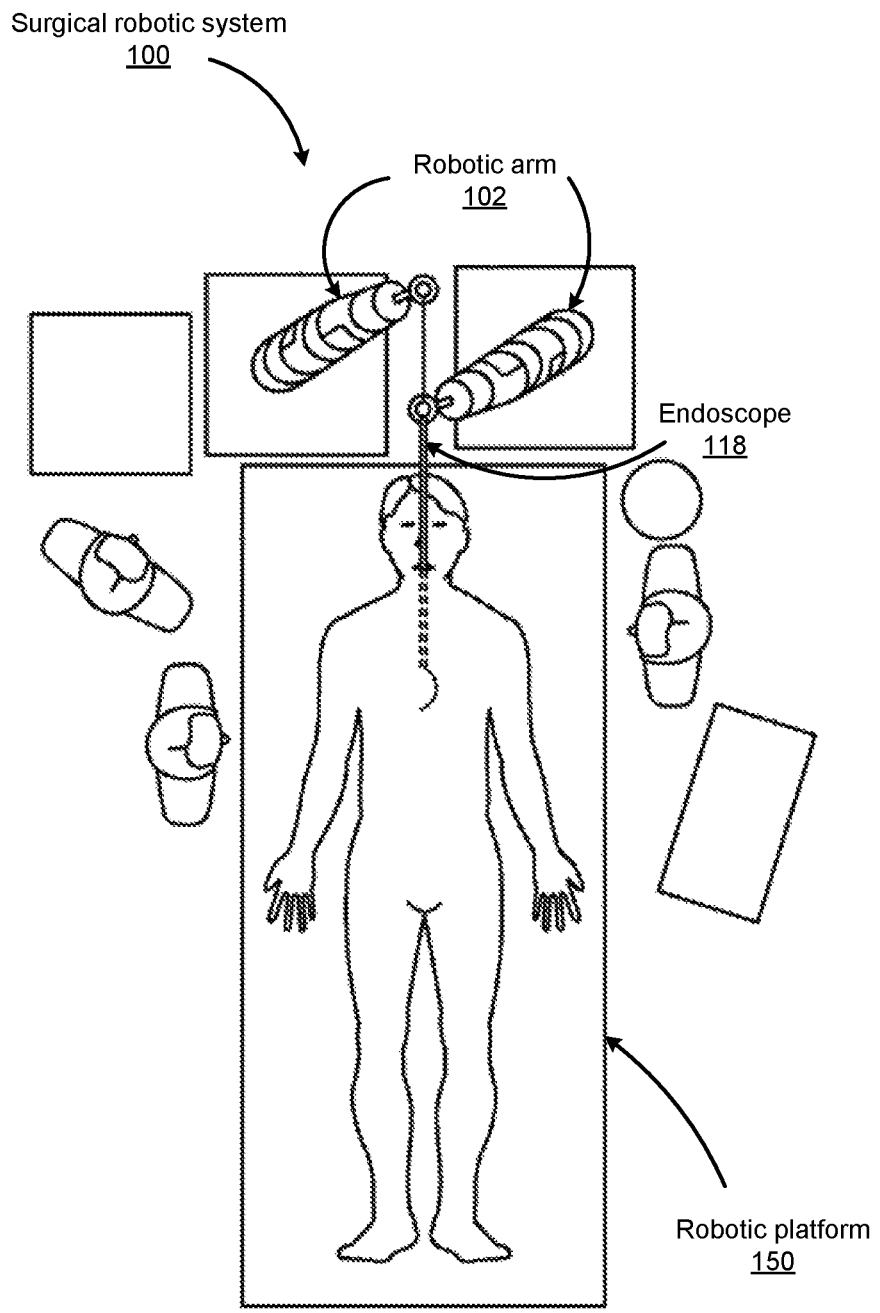
Figure 1D:
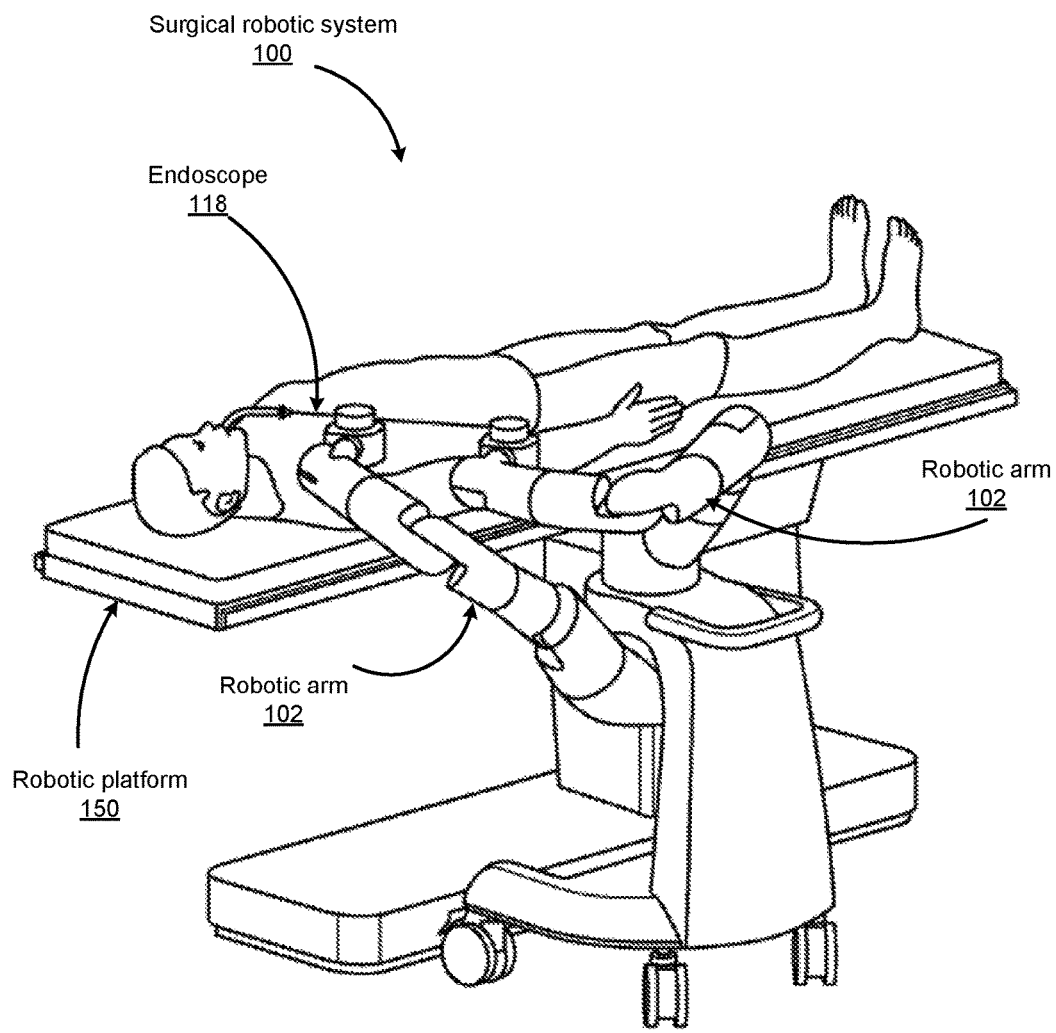
Figure 1E:
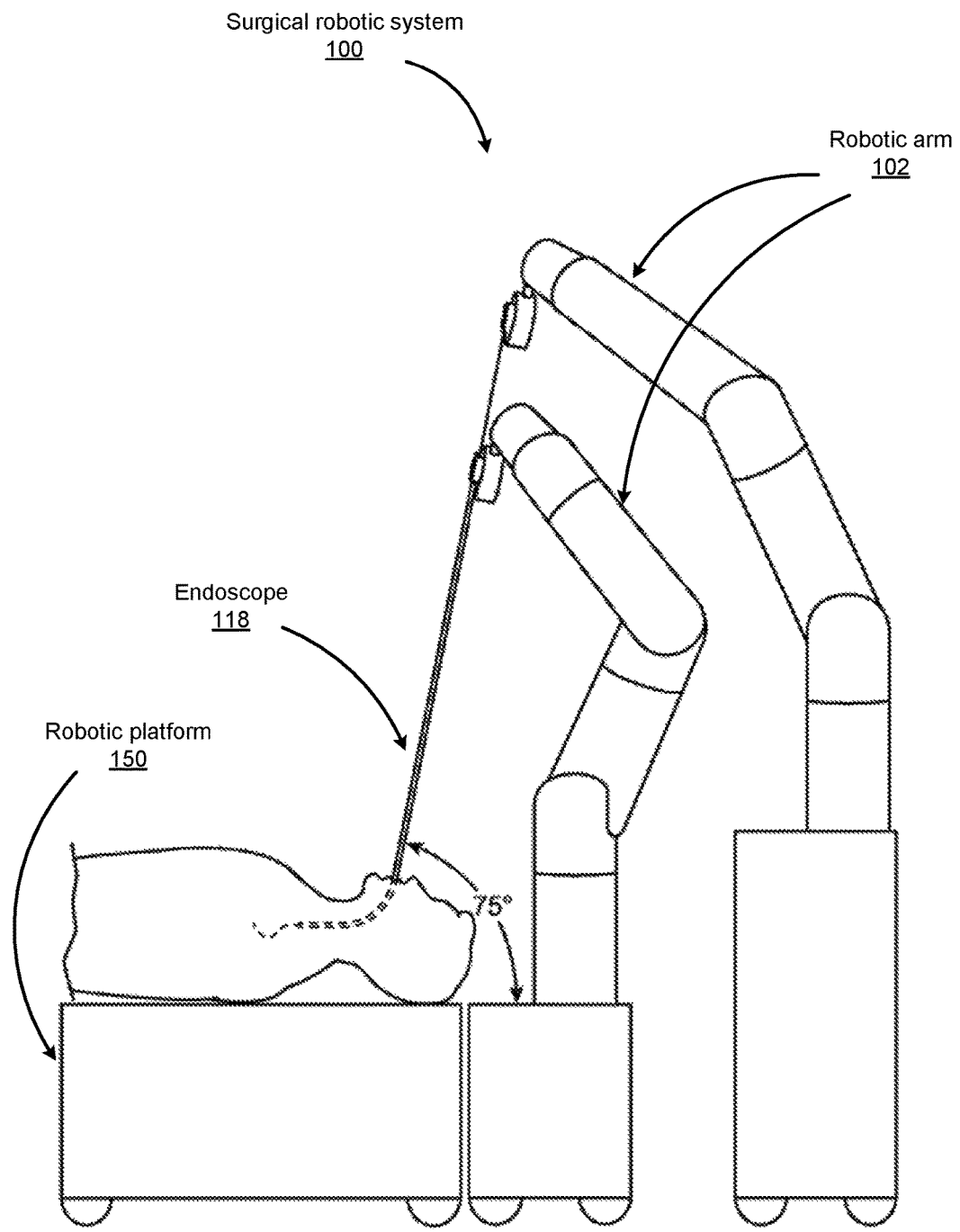
Figure 1F:
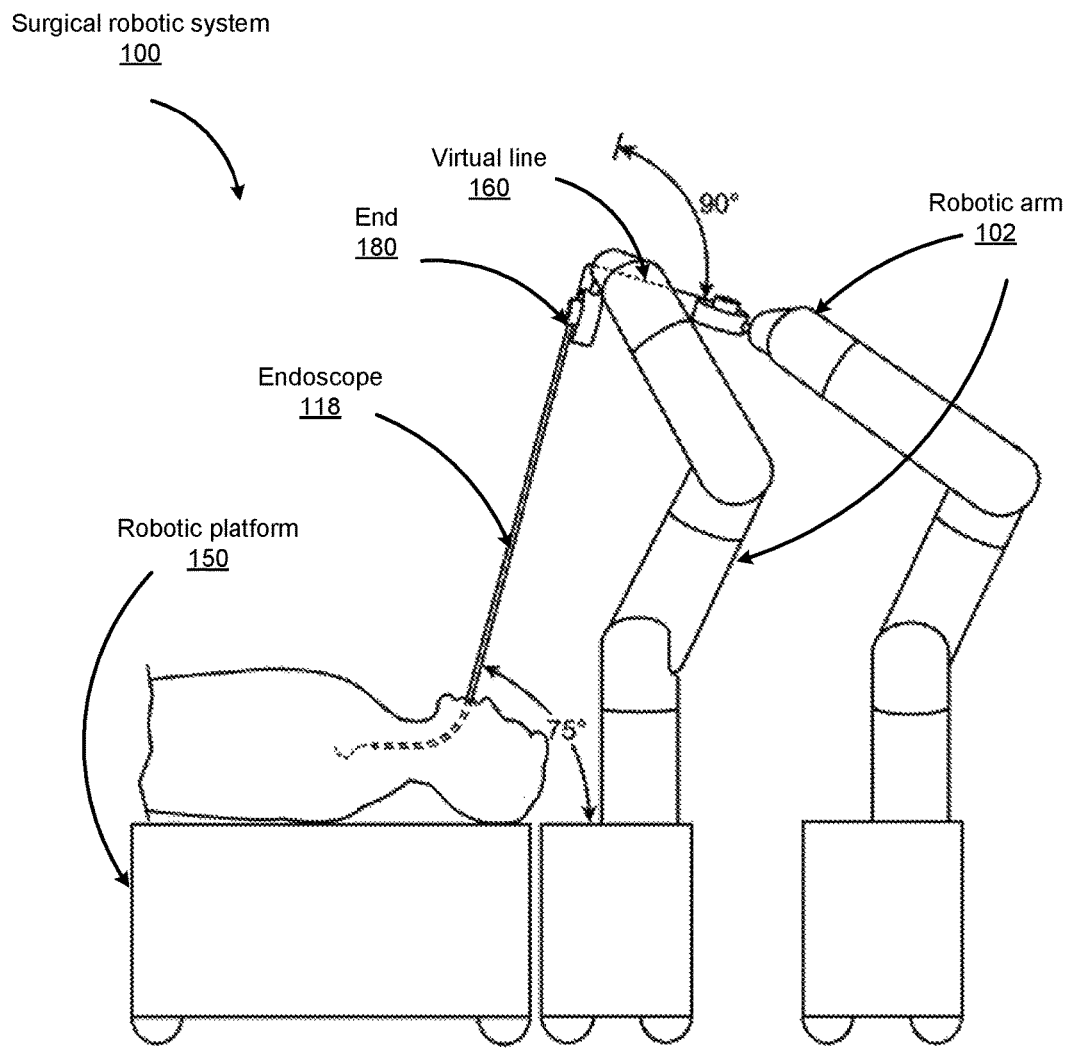

FIGS. 1B-1F show various perspective views of the surgical robotic system 100 coupled to a robotic platform 150 (or surgical bed), according to various embodiments. Specifically, FIG. 1B shows a side view of the surgical robotic system 100 with the robotic arms 102 manipulating the endoscopic 118 to insert the endoscopic inside a patient's body, and the patient is lying on the robotic platform 150. FIG. 1C shows a top view of the surgical robotic system 100 and the robotic platform 150, and the endoscopic 118 manipulated by the robotic arms is inserted inside the patient's body. FIG. 1D shows a perspective view of the surgical robotic system 100 and the robotic platform 150, and the endoscopic 118 is controlled to be positioned horizontally parallel with the robotic platform. FIG. 1E shows another perspective view of the surgical robotic system 100 and the robotic platform 150, and the endoscopic 118 is controlled to be positioned relatively perpendicular to the robotic platform. In more detail, in FIG. 1E, the angle between the horizontal surface of the robotic platform 150 and the endoscopic 118 is 75 degree. FIG. 1F shows the perspective view of the surgical robotic system 100 and the robotic platform 150 shown in FIG. 1E, and in more detail, the angle between the endoscopic 118 and the virtual line 160 connecting one end 180 of the endoscopic and the robotic arm 102 that is positioned relatively farther away from the robotic platform is 90 degree.

II. Command Console

Figure 2:
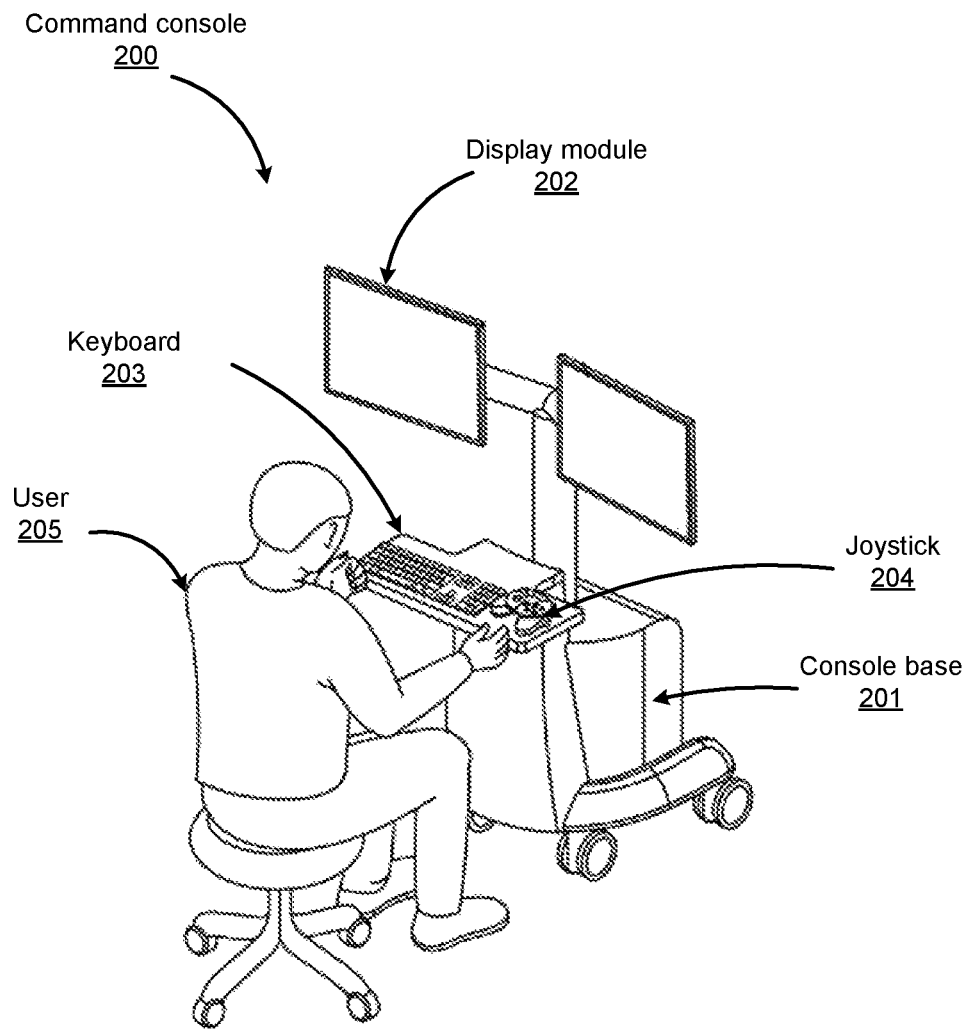
FIG. 2 shows an example command console for the example surgical robotic system, according to one embodiment.

FIG. 2 shows an example command console 200 for the example surgical robotic system 100, according to one embodiment. The command console 200 includes a console base 201, display modules 202, e.g., monitors, and control modules, e.g., a keyboard 203 and joystick 204. In some embodiments, one or more of the command console 200 functionality may be integrated into a base 101 of the surgical robotic system 100 or another system communicatively coupled to the surgical robotic system 100. A user 205, e.g., a physician, remotely controls the surgical robotic system 100 from an ergonomic position using the command console 200.

The console base 201 may include a central processing unit, a memory unit, a data bus, and associated data communication ports that are responsible for interpreting and processing signals such as camera imagery and tracking sensor data, e.g., from the endoscope 118 shown in FIG. 1. In some embodiments, both the console base 201 and the base 101 perform signal processing for load-balancing. The console base 201 may also process commands and instructions provided by the user 205 through the control modules 203 and 204. In addition to the keyboard 203 and joystick 204 shown in FIG. 2, the control modules may include other devices, for example, computer mice, trackpads, trackballs, control pads, video game controllers, and sensors (e.g., motion sensors or cameras) that capture hand gestures and finger gestures.

The user 205 can control a surgical instrument such as the endoscope 118 using the command console 200 in a velocity mode or position control mode. In velocity mode, the user 205 directly controls pitch and yaw motion of a distal end of the endoscope 118 based on direct manual control using the control modules. For example, movement on the joystick 204 may be mapped to yaw and pitch movement in the distal end of the endoscope 118. The joystick 204 can provide haptic feedback to the user 205. For example, the joystick 204 vibrates to indicate that the endoscope 118 cannot further translate or rotate in a certain direction. The command console 200 can also provide visual feedback (e.g., pop-up messages) and/or audio feedback (e.g., beeping) to indicate that the endoscope 118 has reached maximum translation or rotation.

In position control mode, the command console 200 uses a three-dimensional (3D) map of a patient and pre-determined computer models of the patient to control a surgical instrument, e.g., the endoscope 118. The command console 200 provides control signals to robotic arms 102 of the surgical robotic system 100 to manipulate the endoscope 118 to a target location. Due to the reliance on the 3D map, position control mode requires accurate mapping of the anatomy of the patient.

In some embodiments, users 205 can manually manipulate robotic arms 102 of the surgical robotic system 100 without using the command console 200. During setup in a surgical operating room, the users 205 may move the robotic arms 102, endoscopes 118, and other surgical equipment to access a patient. The surgical robotic system 100 may rely on force feedback and inertia control from the users 205 to determine appropriate configuration of the robotic arms 102 and equipment.

The display modules 202 may include electronic monitors, virtual reality viewing devices, e.g., goggles or glasses, and/or other means of display devices. In some embodiments, the display modules 202 are integrated with the control modules, for example, as a tablet device with a touchscreen. Further, the user 205 can both view data and input commands to the surgical robotic system 100 using the integrated display modules 202 and control modules.

The display modules 202 can display 3D images using a stereoscopic device, e.g., a visor or goggle. The 3D images provide an "endo view" (i.e., endoscopic view), which is a computer 3D model illustrating the anatomy of a patient. The "endo view" provides a virtual environment of the patient's interior and an expected location of an endoscope 118 inside the patient. A user 205 compares the "endo view" model to actual images captured by a camera to help mentally orient and confirm that the endoscope 118 is in the correct—or approximately correct—location within the patient. The "endo view" provides information about anatomical structures, e.g., the shape of an intestine or colon of the patient, around the distal end of the endoscope 118. The display modules 202 can simultaneously display the 3D model and computerized tomography (CT) scans of the anatomy the around distal end of the endoscope 118. Further, the display modules 202 may overlay the already determined navigation paths of the endoscope 118 on the 3D model and CT scans.

In some embodiments, a model of the endoscope 118 is displayed with the 3D models to help indicate a status of a surgical procedure. For example, the CT scans identify a lesion in the anatomy where a biopsy may be necessary. During operation, the display modules 202 may show a reference image captured by the endoscope 118 corresponding to the current location of the endoscope 118. The display modules 202 may automatically display different views of the model of the endoscope 118 depending on user settings and a particular surgical procedure. For example, the display modules 202 show an overhead fluoroscopic view of the endoscope 118 during a navigation step as the endoscope 118 approaches an operative region of a patient.

III. Instrument Device Manipulator

Figure 3A:
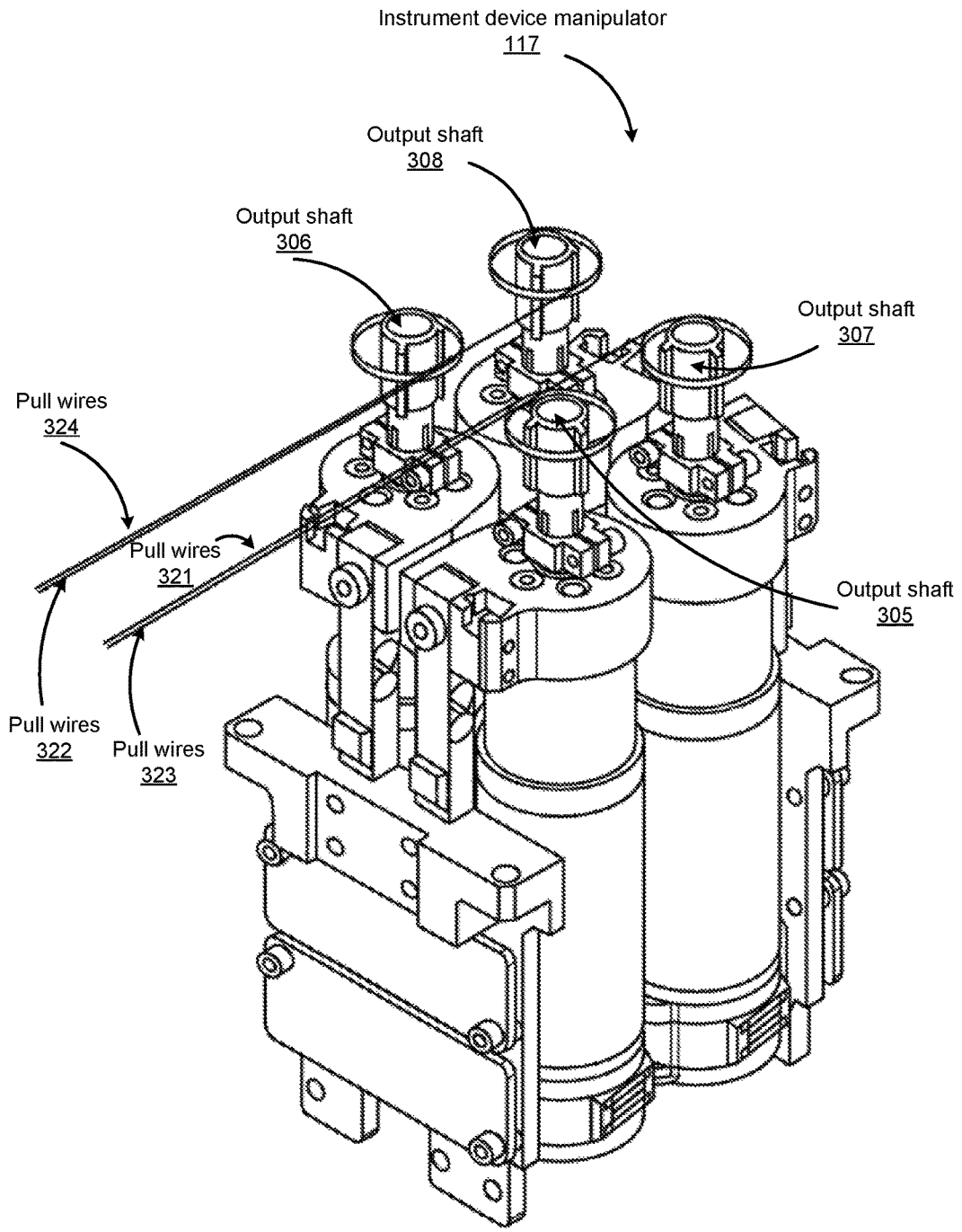
FIG. 3A shows an isometric view of an example independent drive mechanism of the instrument device manipulator (IDM) shown in FIG. 1A, according to one embodiment.

FIG. 3A shows an isometric view of an example independent drive mechanism of the IDM 117 shown in FIG. 1, according to one embodiment. The independent drive mechanism can tighten or loosen the pull wires 321, 322, 323, and 324 (e.g., independently from each other) of an endoscope by rotating the output shafts 305, 306, 307, and 308 of the IDM 117, respectively. Just as the output shafts 305, 306, 307, and 308 transfer force down pull wires 321, 322, 323, and 324, respectively, through angular motion, the pull wires 321, 322, 323, and 324 transfer force back to the output shafts. The IDM 117 and/or the surgical robotic system 100 can measure the transferred force using a sensor, e.g., a strain gauge further described below.

Figure 3B:
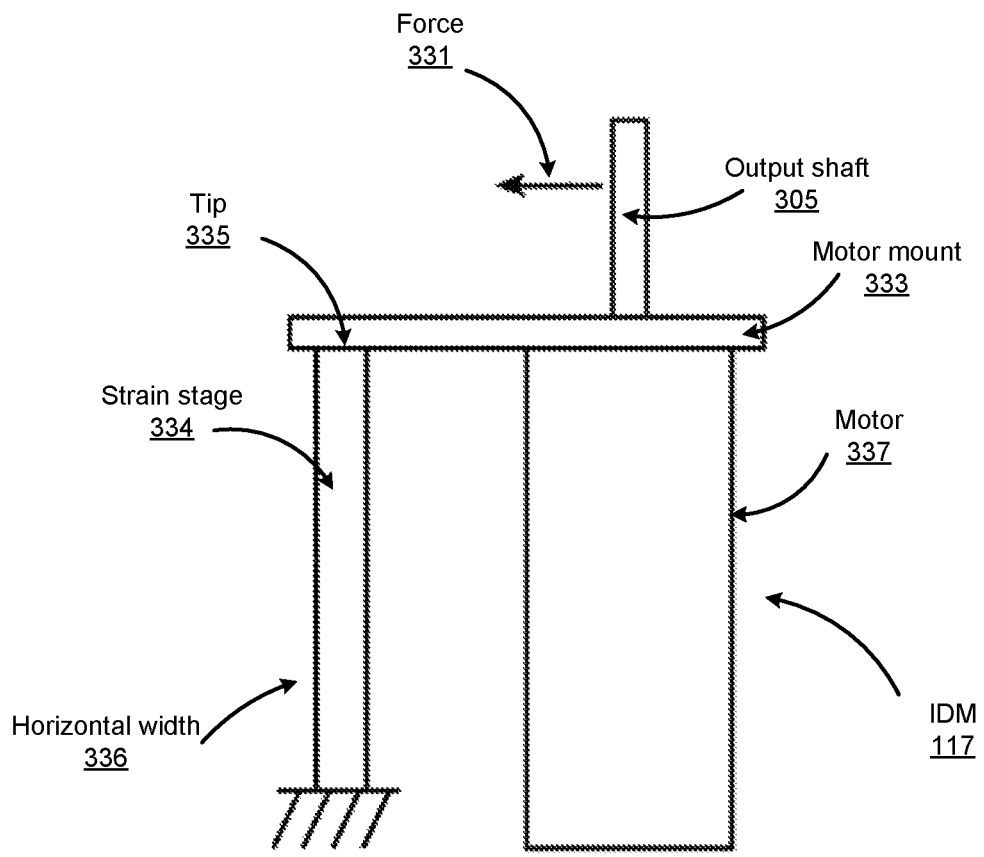
FIG. 3B shows a conceptual diagram that shows how forces may be measured by a strain gauge of the independent drive mechanism shown in FIG. 3A, according to one embodiment.

FIG. 3B shows a conceptual diagram that shows how forces may be measured by a strain gauge 334 of the independent drive mechanism shown in FIG. 3A, according to one embodiment. A force 331 may direct away from the output shaft 305 coupled to the motor mount 333 of the motor 337. Accordingly, the force 331 results in horizontal displacement of the motor mount 333. Further, the strain gauge 334 horizontally coupled to the motor mount 333 experiences strain in the direction of the force 331. The strain may be measured as a ratio of the horizontal displacement of the tip 335 of strain gauge 334 to the overall horizontal width 336 of the strain gauge 334.

In some embodiments, the IDM 117 includes additional sensors, e.g., inclinometers or accelerometers, to determine an orientation of the IDM 117. Based on measurements from the additional sensors and/or the strain gauge 334, the surgical robotic system 100 can calibrate readings from the strain gauge 334 to account for gravitational load effects. For example, if the IDM 117 is oriented on a horizontal side of the IDM 117, the weight of certain components of the IDM 117 may cause a strain on the motor mount 333. Accordingly, without accounting for gravitational load effects, the strain gauge 334 may measure strain that did not result from strain on the output shafts.

IV. Endoscope

Figure 4A:
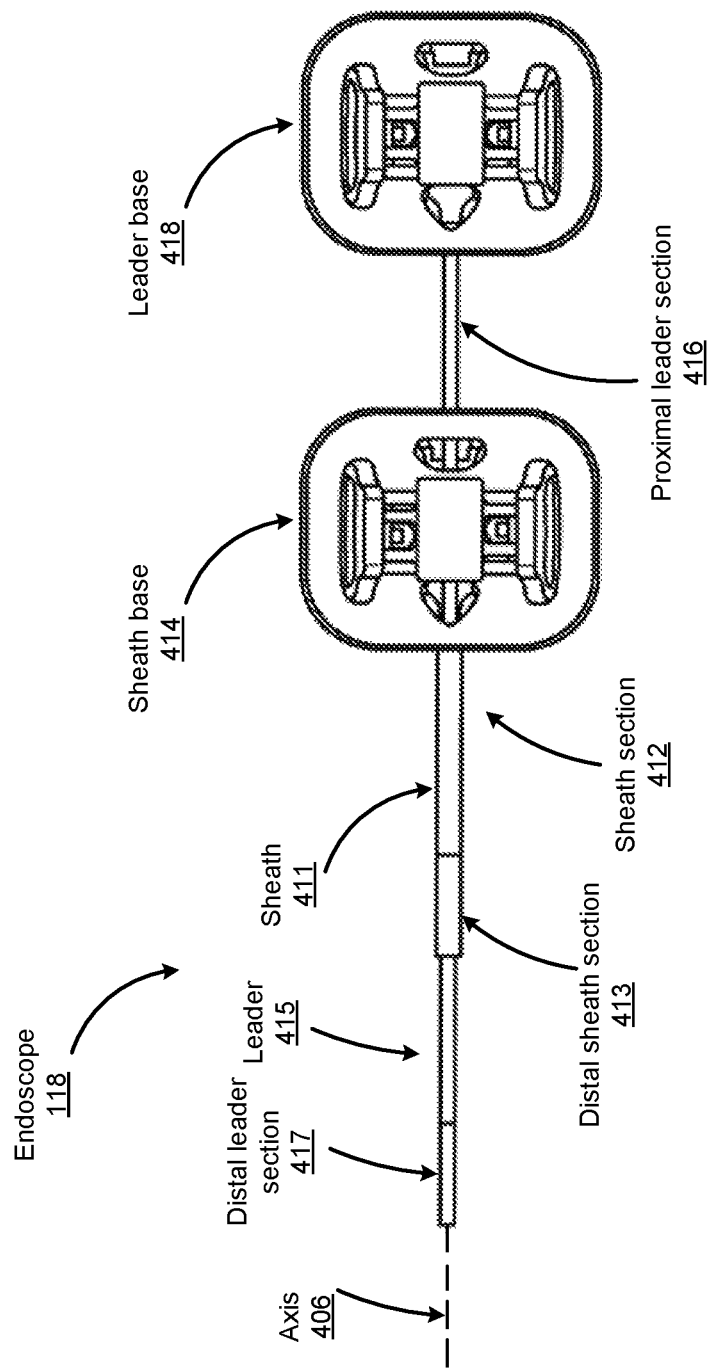
FIG. 4A shows a top view of an example endoscope, according to one embodiment.

FIG. 4A shows a top view of an example endoscope 118, according to one embodiment. The endoscope 118 includes a leader 415 tubular component nested or partially nested inside and longitudinally-aligned with a sheath 411 tubular component. The sheath 411 includes a proximal sheath section 412 and distal sheath section 413. The leader 415 has a smaller outer diameter than the sheath 411 and includes a proximal leader section 416 and distal leader section 417. The sheath base 414 and the leader base 418 actuate the distal sheath section 413 and the distal leader section 417, respectively, for example, based on control signals from a user of a surgical robotic system 100. The sheath base 414 and the leader base 418 are, e.g., part of the IDM 117 shown in FIG. 1.

Both the sheath base 414 and the leader base 418 include drive mechanisms (e.g., the independent drive mechanism further described with reference to FIG. 3A-B in Section III. Instrument Device Manipulator) to control pull wires coupled to the sheath 411 and leader 415. For example, the sheath base 414 generates tensile loads on pull wires coupled to the sheath 411 to deflect the distal sheath section 413. Similarly, the leader base 418 generates tensile loads on pull wires coupled to the leader 415 to deflect the distal leader section 417. Both the sheath base 414 and leader base 418 may also include couplings for the routing of pneumatic pressure, electrical power, electrical signals, or optical signals from IDMs to the sheath 411 and leader 414, respectively. A pull wire may include a steel coil pipe along the length of the pull wire within the sheath 411 or the leader 415, which transfers axial compression back to the origin of the load, e.g., the sheath base 414 or the leader base 418, respectively.

The endoscope 118 can navigate the anatomy of a patient with ease due to the multiple degrees of freedom provided by pull wires coupled to the sheath 411 and the leader 415. For example, four or more pull wires may be used in either the sheath 411 and/or the leader 415, providing eight or more degrees of freedom. In other embodiments, up to three pull wires may be used, providing up to six degrees of freedom. The sheath 411 and leader 415 may be rotated up to 360 degrees along a longitudinal axis 406, providing more degrees of motion. The combination of rotational angles and multiple degrees of freedom provides a user of the surgical robotic system 100 with a user friendly and instinctive control of the endoscope 118.

Figure 4B:
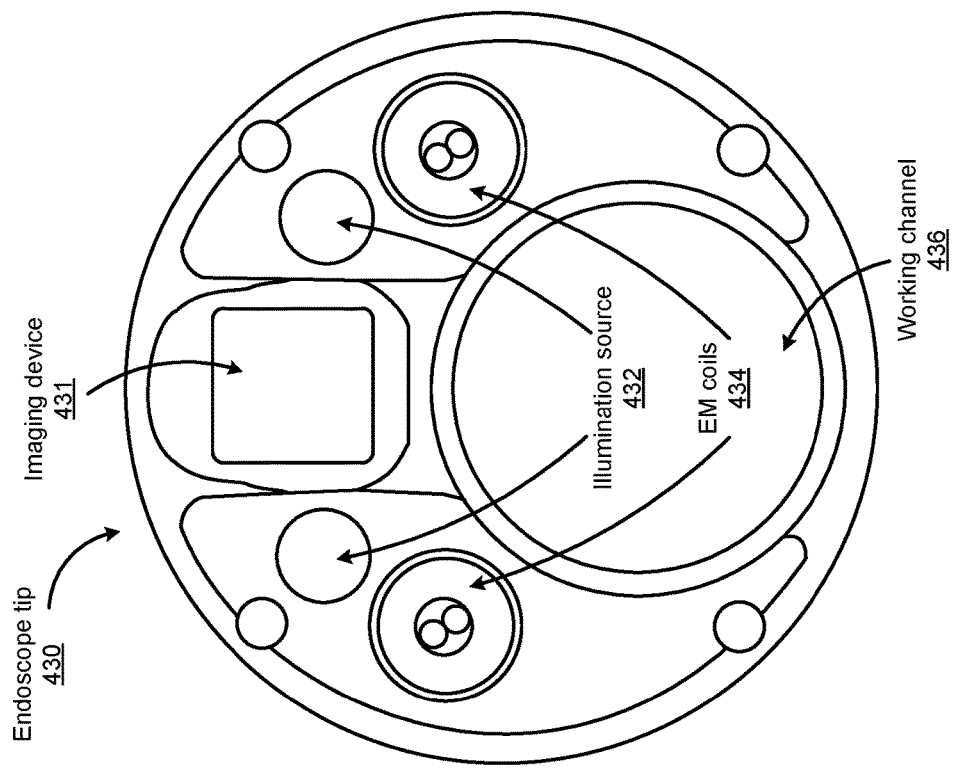
FIG. 4B shows an example endoscope tip of the endoscope shown in FIG. 4A, according to one embodiment.

FIG. 4B illustrates an example endoscope tip 430 of the endoscope 118 shown in FIG. 4A, according to one embodiment. In FIG. 4B, the endoscope tip 430 includes an imaging device 431 (e.g., a camera), illumination sources 432, and ends of EM coils 434. The illumination sources 432 provide light to illuminate an interior portion of an anatomical space. The provided light allows the imaging device 431 to record images of that space, which can then be transmitted to a computer system such as command console 200 for processing as described herein. Electromagnetic coils 434 located on the tip 430 may be used with an electromagnetic tracking system to detect the position and orientation of the endoscope tip 430 while it is disposed within an anatomical system. In some embodiments, the coils may be angled to provide sensitivity to electromagnetic fields along different axes, giving the ability to measure a full 6 degrees of freedom: three positional and three angular. In other embodiments, only a single coil may be disposed within the endoscope tip 430, with its axis oriented along the endoscope shaft of the endoscope 118; due to the rotational symmetry of such a system, it is insensitive to roll about its axis, so only 5 degrees of freedom may be detected in such a case. The endoscope tip 430 further comprises a working channel 436 through which surgical instruments, such as biopsy needles, may be inserted along the endoscope shaft, allowing access to the area near the endoscope tip.

V. Registration Transform of EM System to 3D Model

V. A. Schematic Setup of an EM Tracking System

Figure 5:
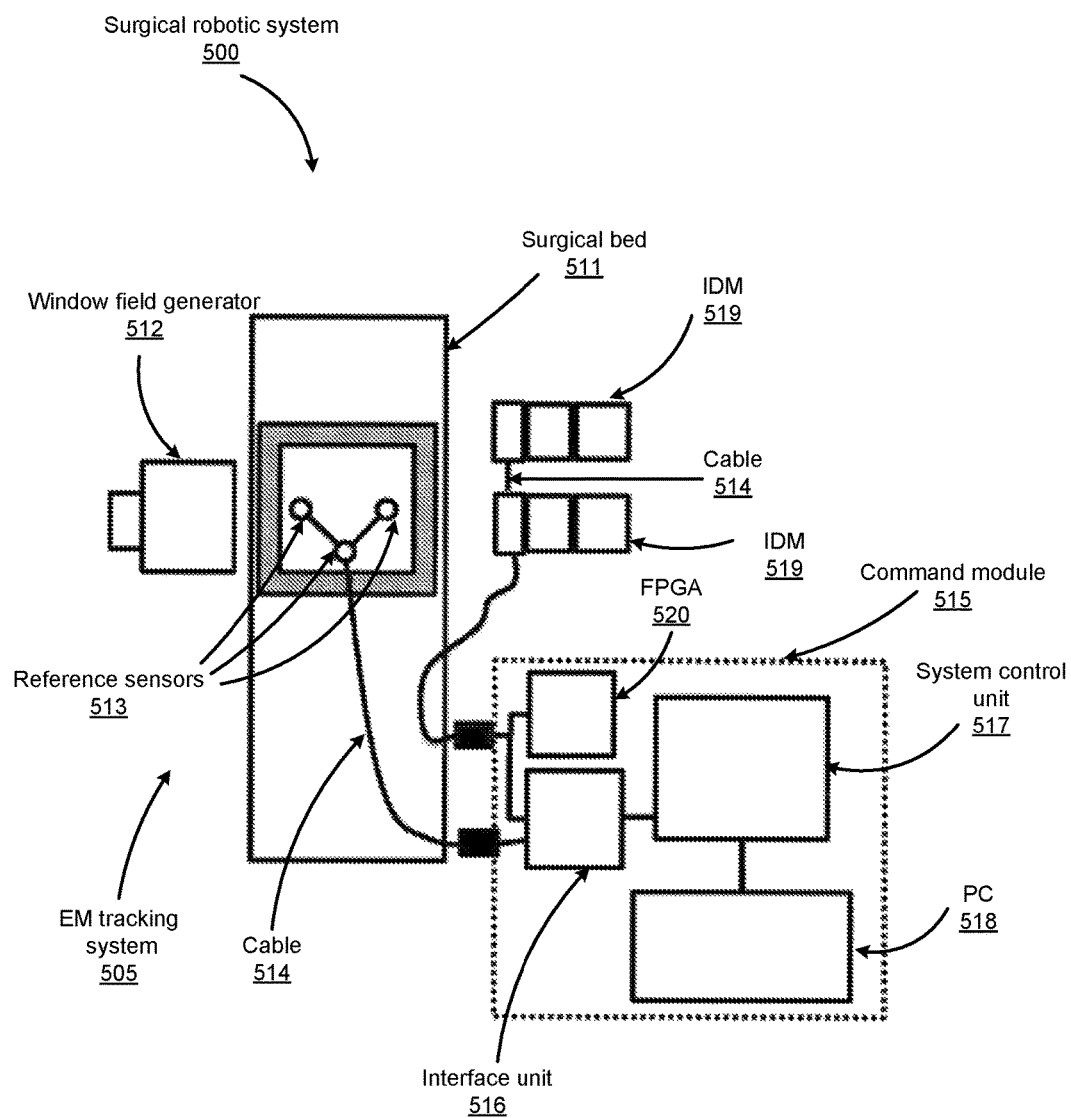
FIG. 5 shows an example schematic setup of an EM tracking system included in a surgical robotic system, according to one embodiment.

FIG. 5 shows an example schematic setup of an EM tracking system 505 included in a surgical robotic system 500, according to one embodiment. In FIG. 5, multiple robot components (e.g., window field generator, reference sensors as described below) are included in the EM tracking system 505. The robotic surgical system 500 includes a surgical bed 511 to hold a patient's body. Beneath the bed 511 is the window field generator (WFG) 512 configured to sequentially activate a set of EM coils (e.g., the EM coils 434 shown in FIG. 4B). The WFG 512 generates an alternating current (AC) magnetic field over a wide volume; for example, in some cases it may create an AC field in a volume of about 0.5×0.5×0.5 m.

Additional fields may be applied by further field generators to aid in tracking instruments within the body. For example, a planar field generator (PFG) may be attached to a system arm adjacent to the patient and oriented to provide an EM field at an angle. Reference sensors 513 may be placed on the patient's body to provide local EM fields to further increase tracking accuracy. Each of the reference sensors 513 may be attached by cables 514 to a command module 515. The cables 514 are connected to the command module 515 through interface units 516 which handle communications with their respective devices as well as providing power. The interface unit 516 is coupled to a system control unit (SCU) 517 which acts as an overall interface controller for the various entities mentioned above. The SCU 517 also drives the field generators (e.g., WFG 512), as well as collecting sensor data from the interface units 516, from which it calculates the position and orientation of sensors within the body. The SCU 517 may be coupled to a personal computer (PC) 518 to allow user access and control.

The command module 515 is also connected to the various IDMs 519 coupled to the surgical robotic system 500 as described herein. The IDMs 519 are typically coupled to a single surgical robotic system (e.g., the surgical robotic system 500) and are used to control and receive data from their respective connected robotic components; for example, robotic endoscope tools or robotic arms. As described above, as an example, the IDMs 519 are coupled to an endoscopic tool (not shown here) of the surgical robotic system 500

The command module 515 receives data passed from the endoscopic tool. The type of received data depends on the corresponding type of instrument attached. For example, example received data includes sensor data (e.g., image data, EM data), robot data (e.g., endoscopic and IDM physical motion data), control data, and/or video data. To better handle video data, a field-programmable gate array (FPGA) 520 may be configured to handle image processing. Comparing data obtained from the various sensors, devices, and field generators allows the SCU 517 to precisely track the movements of different components of the surgical robotic system 500, and for example, positions and orientations of these components.

In order to track a sensor through the patient's anatomy, the EM tracking system 505 may require a process known as "registration," where the system finds the geometric transformation that aligns a single object between different coordinate systems. For instance, a specific anatomical site on a patient has two different representations in the 3D model coordinates and in the EM sensor coordinates. To be able to establish consistency and common language between these two different coordinate systems, the EM tracking system 505 needs to find the transformation that links these two representations, i.e., registration. For example, the position of the EM tracker relative to the position of the EM field generator may be mapped to a 3D coordinate system to isolate a location in a corresponding 3D model.

V. B. 3D Model Representation

Figure 6A:
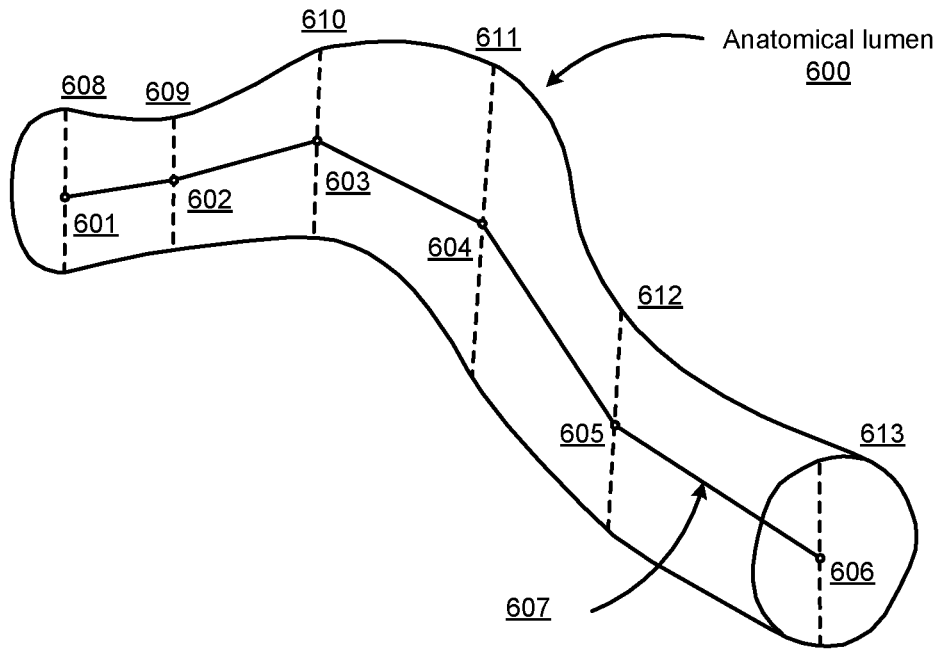
FIGS. 6A-6B show an example anatomical lumen and an example 3D model of the anatomical lumen, according to one embodiment.
Figure 6B:
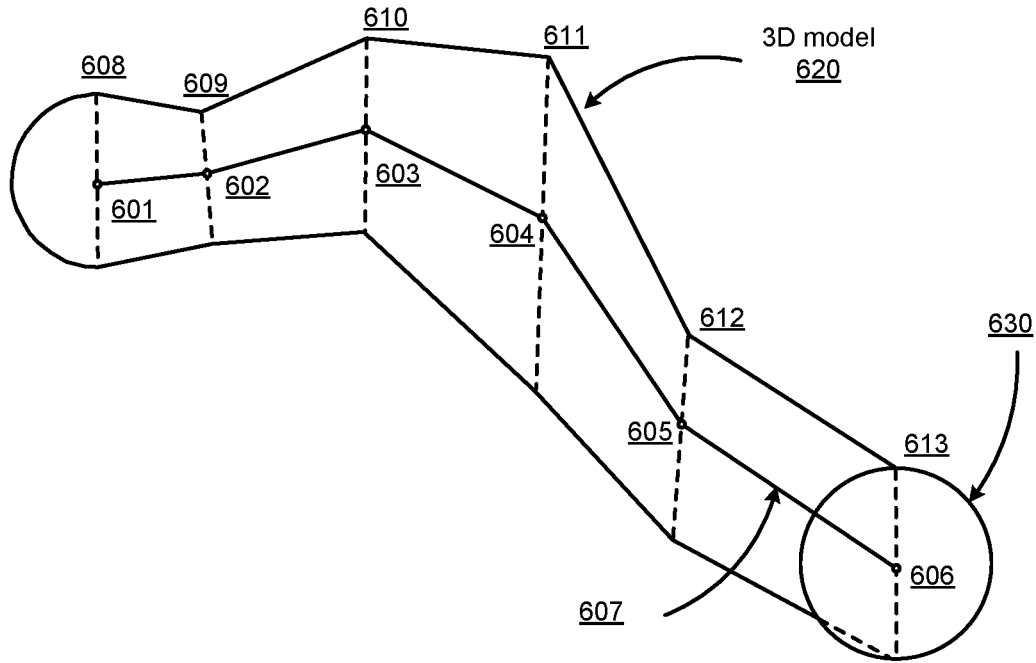

FIGS. 6A-6B show an example anatomical lumen 600 and an example 3D model 620 of the anatomical lumen, according to one embodiment. More specifically, FIGS. 6A-6B illustrate relationship of centerline coordinates, diameter measurements and anatomical spaces between the actual anatomical lumen 600 and its 3D model 620. In FIG. 6A, the anatomical lumen 600 is roughly tracked longitudinally by centerline coordinates 601, 602, 603, 604, 605, and 606 where each centerline coordinate roughly approximates the center of the tomographic slice of the lumen. The centerline coordinates are connected and visualized by a centerline 607. The volume of the lumen can be further visualized by measuring the diameter of the lumen at each centerline coordinate, e.g., coordinates 608, 609, 610, 611, 612, and 613 represent the measurements of the lumen 600 corresponding to coordinates 601, 602, 603, 604, 605, and 606.

FIG. 6B shows the example 3D model 620 of the anatomical lumen 600 shown in FIG. 6A, according to one embodiment. In FIG. 6B, the anatomical lumen 600 is visualized in 3D space by first locating the centerline coordinates 601, 602, 603, 604, 605, and 606 in 3D space based on the centerline 607. As one example, at each centerline coordinate, the lumen diameter is visualized as a 2D circular space (e.g., the 2D circular space 630) with diameters 608, 609, 610, 611, 612, and 613. By connecting those 2D circular spaces to form a 3D space, the anatomical lumen 600 is approximated and visualized as the 3D model 620. More accurate approximations may be determined by increasing the resolution of the centerline coordinates and measurements, i.e., increasing the density of centerline coordinates and measurements for a given lumen or subsection. Centerline coordinates may also include markers to indicate point of interest for the physician, including lesions.

In some embodiments, a pre-operative software package is also used to analyze and derive a navigation path based on the generated 3D model of the anatomical space. For example, the software package may derive a shortest navigation path to a single lesion (marked by a centerline coordinate) or to several lesions. This navigation path may be presented to the operator intra-operatively either in two-dimensions or three-dimensions depending on the operator's preference.

Figure 7:
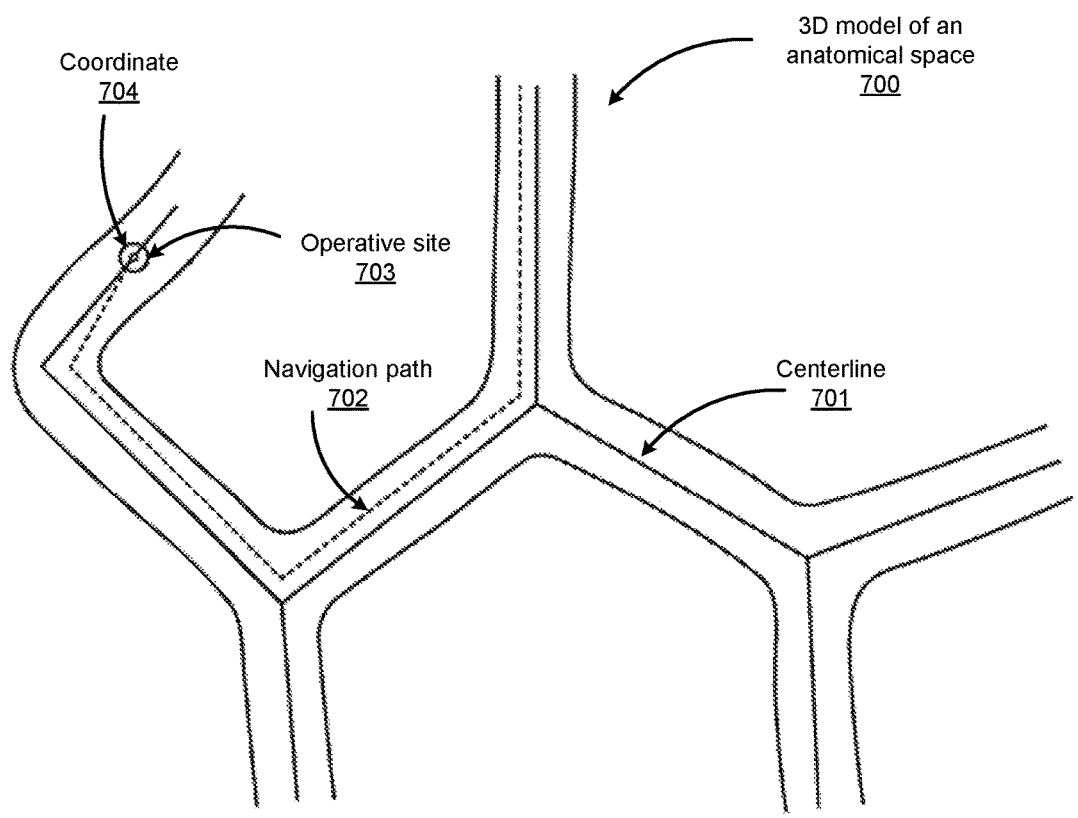
FIG. 7 shows a computer-generated 3D model representing an anatomical space, according to one embodiment.

FIG. 7 shows a computer-generated 3D model 700 representing an anatomical space, according to one embodiment. As discussed above in FIGS. 6A-6B, the 3D model 700 may be generated using centerline 701 that was obtained by reviewing CT scans that were generated preoperatively. In some embodiments, computer software may be able to map the navigation path 702 within the tubular network to access an operative site 703 within the 3D model 700. In some embodiments, the operative site 703 may be linked to an individual centerline coordinate 704, which allows a computer algorithm to topologically search the centerline coordinates of the 3D model 700 for the optimum path 702 within the tubular network.

In some embodiments, the distal end of the endoscopic tool within the patient's anatomy is tracked, and the tracked location of the endoscopic tool within the patient's anatomy is mapped and placed within a computer model, which enhances the navigational capabilities of the tubular network. In order to track the distal working end of the endoscopic tool, i.e., location and orientation of the working end, a number of approaches may be employed, either individually or in combination.

In a sensor-based approach to localization, a sensor, such as an electromagnetic (EM) tracker, may be coupled to the distal working end of the endoscopic tool to provide a real-time indication of the progression of the endoscopic tool. In EM-based tracking, an EM tracker, embedded in the endoscopic tool, measures the variation in the electromagnetic field created by one or more EM transmitters. The transmitters (or field generators), may be placed close to the patient (e.g., as part of the surgical bed) to create a low intensity magnetic field. This induces small-currents in sensor coils in the EM tracker, which are correlated to the distance and angle between the sensor and the generator. The electrical signal may then be digitized by an interface unit (on-chip or PCB) and sent via cables/wiring back to the system cart and then to the command module. The data may then be processed to interpret the current data and calculate the precise location and orientation of the sensor relative to the transmitters. Multiple sensors may be used at different locations in the endoscopic tool, for instance in leader and sheath in order to calculate the individual positions of those components. Accordingly, based on readings from an artificially-generated EM field, the EM tracker may detect changes in field strength as it moves through the patient's anatomy.

V. C. On-the-Fly Electromagnetic Registration

Figure 8A:
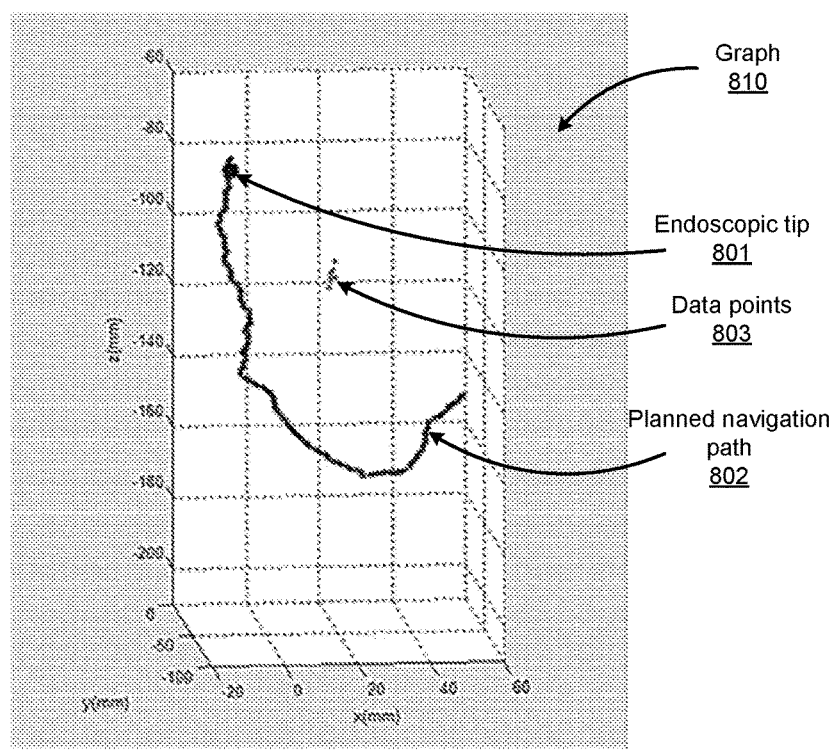
FIGS. 8A-8D show example graphs illustrating on-the-fly registration of an EM system to a 3D model of a path through a tubular network, according to one embodiment.

FIGS. 8A-8D show example graphs 810-840 illustrating on-the-fly registration of an EM system to a 3D model of a path through a tubular network, according to one embodiment. The navigation configuration system described herein allows for on-the-fly registration of the EM coordinates to the 3D model coordinates without the need for independent registration prior to an endoscopic procedure. In more detail, FIG. 8A shows that the coordinate systems of the EM tracking system and the 3D model are initially not registered to each other, and the graph 810 in FIG. 8A shows the registered (or expected) location of an endoscope tip 801 moving along a planned navigation path 802 through a branched tubular network (not shown here), and the registered location of the instrument tip 801 as well as the planned path 802 are derived from the 3D model. The actual position of the tip is repeatedly measured by the EM tracking system 505, resulting in multiple measured location data points 803 based on EM data. As shown in FIG. 8A, the data points 803 derived from EM tracking are initially located far from the registered location of the endoscope tip 801 expected from the 3D model, reflecting the lack of registration between the EM coordinates and the 3D model coordinates. There may be several reasons for this, for example, even if the endoscope tip is being moved relatively smoothly through the tubular network, there may still be some visible scatter in the EM measurement, due to breathing movement of the lungs of the patient.

The points on the 3D model may also be determined and adjusted based on correlation between the 3D model itself, image data received from optical sensors (e.g., cameras) and robot data from robot commands. The 3D transformation between these points and collected EM data points will determine the initial registration of the EM coordinate system to the 3D model coordinate system.

Figure 8B:
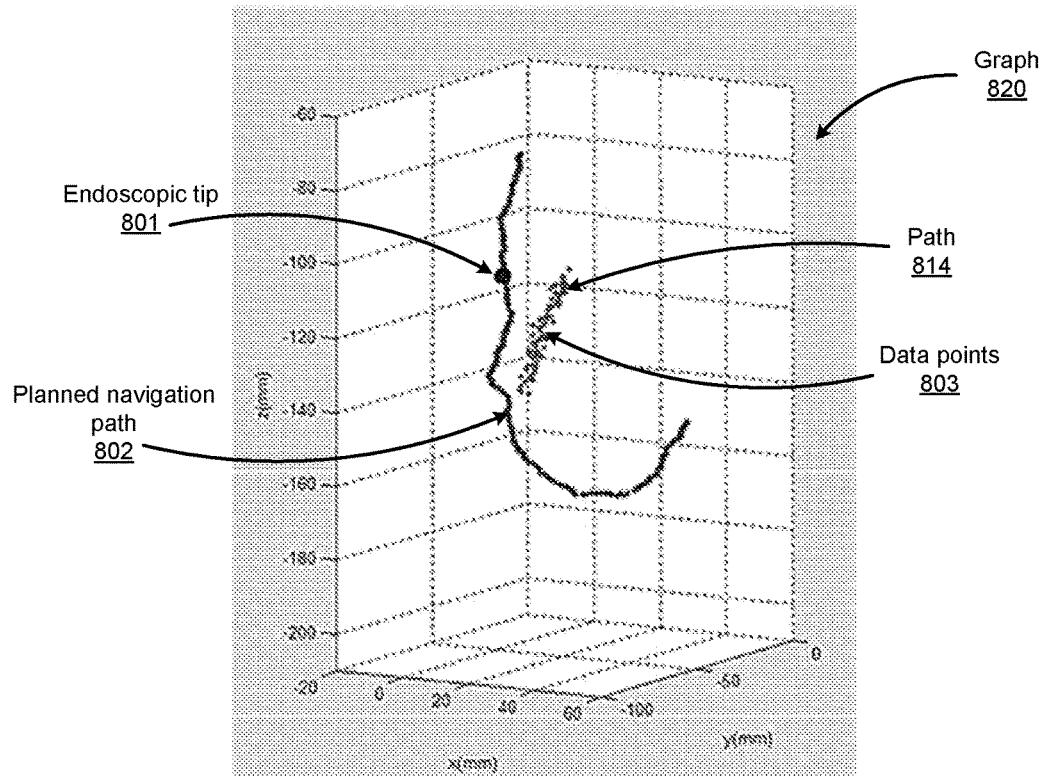

FIG. 8B shows a graph 820 at a later temporal stage compared with the graph 810, according to one embodiment. More specifically, the graph 820 shows the expected location of the endoscope tip 801 expected from the 3D model has been moved farther along the preplanned navigation path 802, as illustrated by the shift from the original expected position of the instrument tip 801 shown in FIG. 8A along the path to the position shown in FIG. 8B. During the EM tracking between generation of the graph 810 and generation of graph 820, additional data points 803 have been recorded by the EM tracking system but the registration has not yet been updated based on the newly collected EM data. As a result, the data points 803 in FIG. 8B are clustered along a visible path 814, but that path differs in location and orientation from the planned navigation path 802 the endoscope tip is being directed by the operator to travel along. Eventually, once sufficient data (e.g., EM data) is accumulated, compared with using only the 3D model or only the EM data, a relatively more accurate estimate can be derived from the transform needed to register the EM coordinates to those of the 3D model. The determination of sufficient data may be made by threshold criteria such as total data accumulated or number of changes of direction. For example, in a branched tubular network such as a bronchial tube network, it may be judged that sufficient data have been accumulated after arriving at two branch points.

Figure 8C:
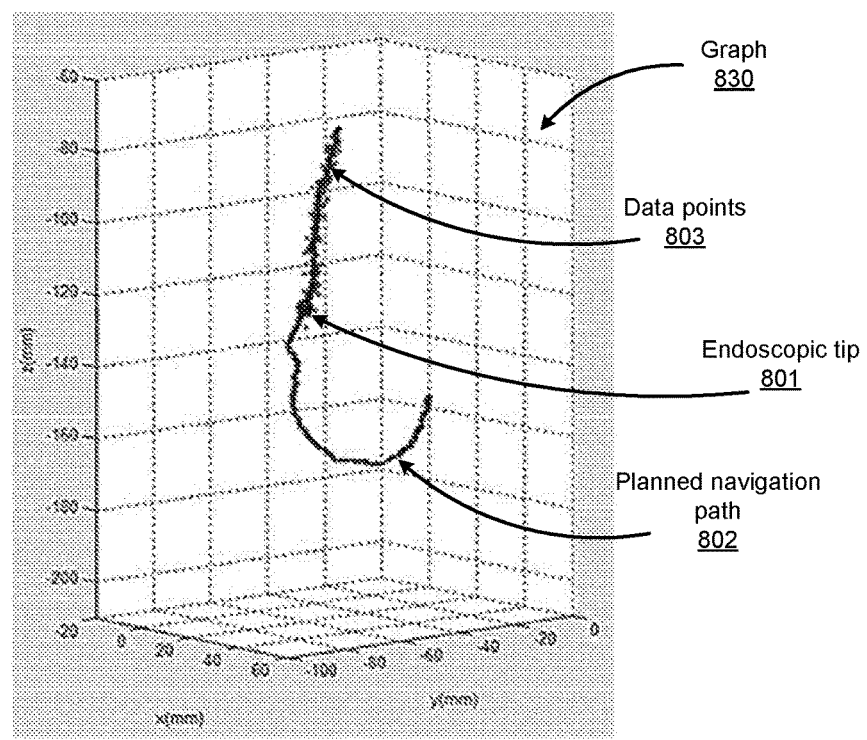

FIG. 8C shows a graph 830 shortly after the navigation configuration system has accumulated a sufficient amount of data to estimate the registration transform from EM to 3D model coordinates, according to one embodiment. The data points 803 in FIG. 8C have now shifted from their previous position as shown in FIG. 8B as a result of the registration transform. As shown in FIG. 8C, the data points 803 derived from EM data is now falling along the planned navigation path 802 derived from the 3D model, and each data point among the data points 803 is now reflecting a measurement of the expected position of endoscope tip 801 in the coordinate system of the 3D model. In some embodiments, as further data are collected, the registration transform may be updated to increase accuracy. In some cases, the data used to determine the registration transformation may be a subset of data chosen by a moving window, so that the registration may change over time, which gives the ability to account for changes in the relative coordinates of the EM and 3D models—for example, due to movement of the patient.

Figure 8D:
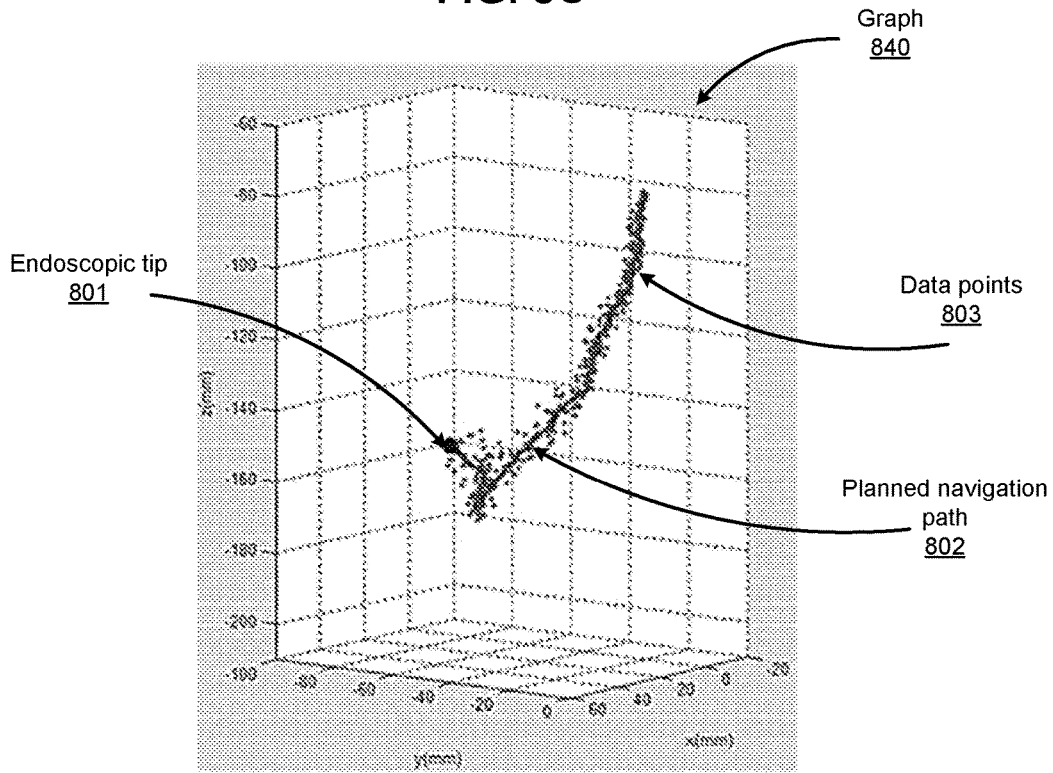

FIG. 8D shows an example graph 840 in which the expected location of the endoscope tip 801 has reached the end of the planned navigation path 802, arriving at the target location in the tubular network, according to one embodiment. As shown in FIG. 8D, the recorded EM data points 803 is now generally tracks along the planned navigation path 802, which represents the tracking of the endoscope tip throughout the procedure. Each data point reflects a transformed location due to the updated registration of the EM tracking system to the 3D model.

In some embodiments, each of the graphs shown in FIGS. 8A-8D can be shown sequentially on a display visible to a user as the endoscope tip is advanced in the tubular network. In some embodiments, the processor can be configured with instructions from the navigation configuration system such that the model shown on the display remains substantially fixed when the measured data points are registered to the display by shifting of the measured path shown on the display in order to allow the user to maintain a fixed frame of reference and to remain visually oriented on the model and on the planned path shown on the display.

Figure 8F:
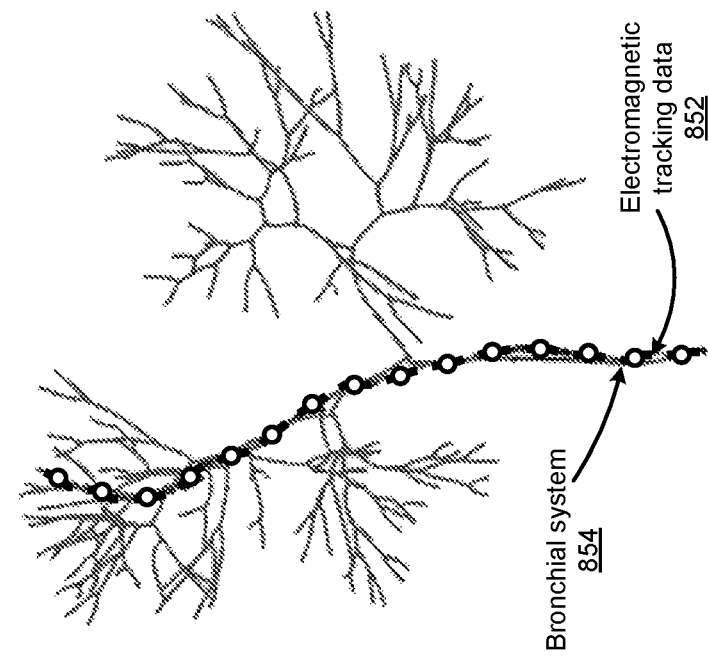
FIGS. 8E-8F show effect of an example registration of the EM system to a 3D model of a branched tubular network, according to one embodiment.
Figure 8E:
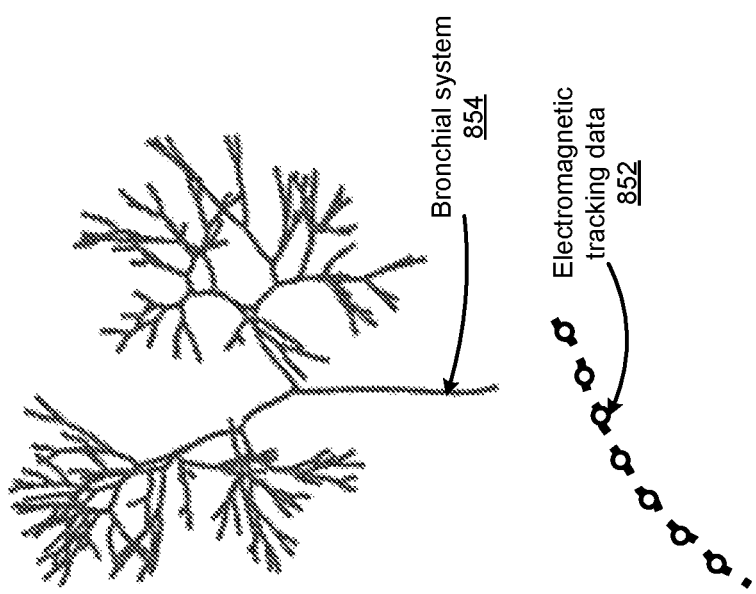

FIGS. 8E-8F show effect of an example registration of the EM system to a 3D model of a branched tubular network, according to one embodiment. In FIGS. 8E-8F, 3D graphs showing electromagnetic tracking data 852 and a model of a patient's bronchial system 854 are illustrated without (shown in FIG. 8E) and with (shown in FIG. 8F) a registration transform. In FIG. 8E, without registration, tracking data 860 have a shape that corresponds to a path through the bronchial system 854, but that shape is subjected to an arbitrary offset and rotation. In FIG. 8F, by applying the registration, the tracking data 852 are shifted and rotated, so that they correspond to a path through the bronchial system 854.

V. D. Mathematical Analysis of Registration Transform

In terms of detailed analysis (e.g., mathematical analysis) and methods of the registration, in some embodiments, a registration matrix can be used to perform the registration between the EM tracking system and the 3D model, and as one example, the matrix may represent a translation and rotation in 6 dimensions. In alternative embodiments, a rotational matrix and a translation vector can be used for performing the registration.

$$M_1(\theta) = \begin{pmatrix} 1 & 0 & 0 \\ 0 & \cos\theta & \sin\theta \\ 0 & -\sin\theta & \cos\theta \end{pmatrix}$$

$$M_2(\varphi) = \begin{pmatrix} \cos\varphi & 0 & -\sin\varphi \\ 0 & 1 & 0 \\ \sin\varphi & 0 & \cos\varphi \end{pmatrix}$$

$$M_3(\psi) = \begin{pmatrix} \cos\psi & \sin\psi & 0 \\ -\sin\psi & \cos\psi & 0 \\ 0 & 0 & 1 \end{pmatrix}$$

From a perspective view of mathematical reasoning, as one example, applying a registration transform involves a shift from one coordinate system (x,y,z) to a new coordinate system (x',y',z') that may in general have its axes rotated to a different 3D orientation as well as having its origin shifted an arbitrary amount in each dimension. For example, a rotation to an azimuthal angle of radians $\theta$ may be expressed by the matrix $M_1$, a rotation to an inclination angle of $\varphi$ radians may be expressed by the matrix $M_2$ etc., and further rotational matrices may be written as the product of rotation matrices. Similarly, a translation vector of ($\Delta$x $\Delta$y $\Delta$z) may be chosen to represent a translation of the origin in the x, y and z axes by $\Delta$x, $\Delta$y, and $\Delta$z respectively.

The registration transform may be determined by such methods as singular value decomposition on a cross correlation matrix between measured EM positions and estimated positions in the 3D model. The transformation matrix components may then be extracted from the decomposition, e.g., by identifying the appropriate principle components. An error signal may also be generated from the residuals of the determined transform, and the size of the error signal may be used to determine a level of confidence in the position. As further data are taken and the registration transform is determined more accurately, this error signal may decrease, indicating an increasing confidence in positions estimated in this manner.

VI. Navigation Configuration System

VI. A. High-Level Overview of Navigation Configuration System

Figure 9A:
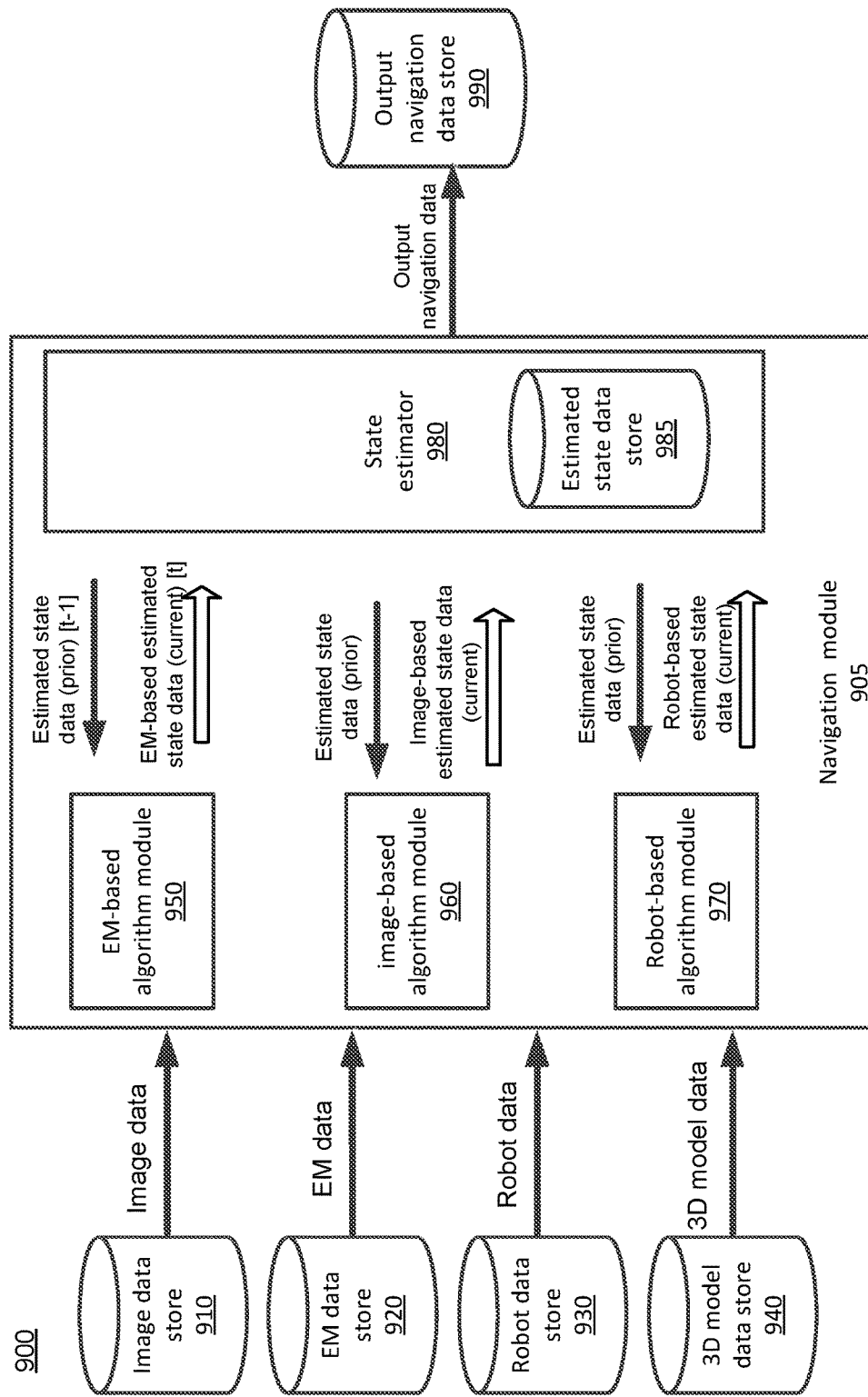
FIG. 9A shows a high-level overview of an example block diagram of a navigation configuration system, according to one embodiment.
Figure 9B:
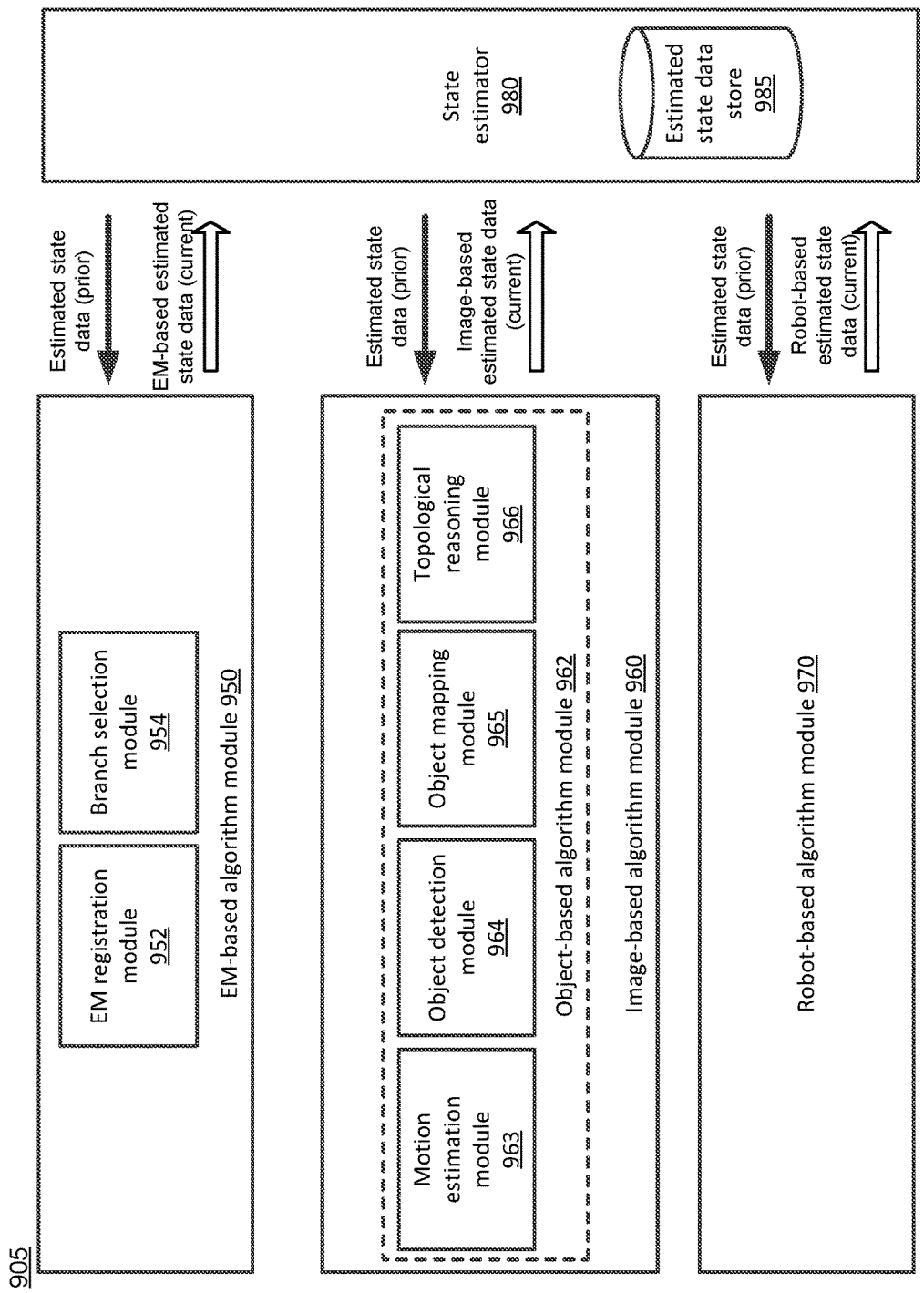
FIG. 9B shows an example block diagram of the navigation module shown in FIG. 9A, according to one embodiment.
Figure 9C:
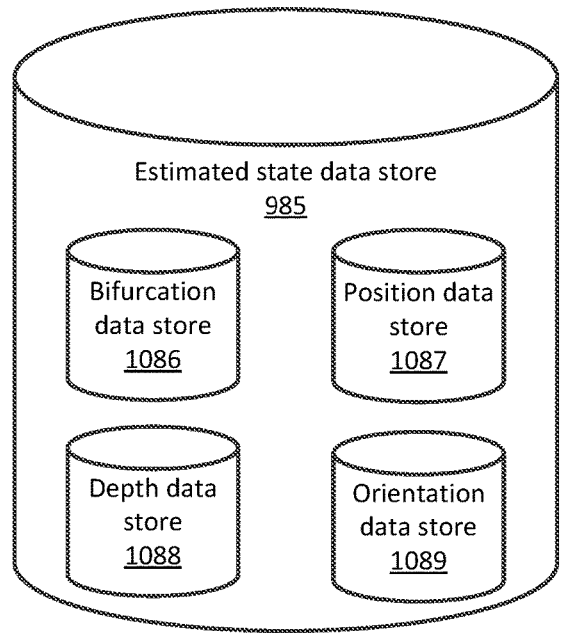
FIG. 9C shows an example block diagram of the estimated state data store included in the state estimator, according to one embodiment.

FIGS. 9A-9C show example block diagrams of a navigation configuration system 900, according to one embodiment. More specifically, FIG. 9A shows a high-level overview of an example block diagram of the navigation configuration system 900, according to one embodiment. In FIG. 9A, the navigation configuration system 900 includes multiple input data stores, a navigation module 905 that receives various types of input data from the multiple input data stores, and an output navigation data store 990 that receives output navigation data from the navigation module. The block diagram of the navigation configuration system 900 shown in FIG. 9A is merely one example, and in alternative embodiments not shown, the navigation configuration system 900 can include different and/or addition entities. Likewise, functions performed by various entities of the system 900 may differ according to different embodiments.

The input data, as used herein, refers to raw data gathered from and/or processed by input devices (e.g., command module, optical sensor, EM sensor, IDM) for generating estimated state information for the endoscope as well as output navigation data. The multiple input data stores 910-940 include an image data store 910, an EM data store 920, a robot data store 930, and a 3D model data store 940. Each type of the input data stores stores the name-indicated type of data for access and use by the navigation module 905. Image data may include one or more image frames captured by the imaging device at the instrument tip, as well as information such as frame rates or timestamps that allow a determination of the time elapsed between pairs of frames. Robot data includes data related to physical movement of the medical instrument or part of the medical instrument (e.g., the instrument tip or sheath) within the tubular network. Example robot data includes command data instructing the instrument tip to reach a specific anatomical site and/or change its orientation (e.g., with a specific pitch, roll, yaw, insertion, and retraction for one or both of a leader and a sheath) within the tubular network, insertion data representing insertion movement of the part of the medical instrument (e.g., the instrument tip or sheath), IDM data, and mechanical data representing mechanical movement of an elongate member of the medical instrument, for example motion of one or more pull wires, tendons or shafts of the endoscope that drive the actual movement of the medial instrument within the tubular network. EM data is collected by EM sensors and/or the EM tracking system as described above. 3D model data is derived from 2D CT scans as described above.

The output navigation data store 990 receives and stores output navigation data provided by the navigation module 905. Output navigation data indicates information to assist in directing the medical instrument through the tubular network to arrive at a particular destination within the tubular network, and is based on estimated state information for the medical instrument at each instant time, the estimated state information including the location and orientation of the medical instrument within the tubular network. In one embodiment, as the medical instrument moves inside the tubular network, the output navigation data indicating updates of movement and location/orientation information of the medical instrument is provided in real time, which better assists its navigation through the tubular network.

To determine the output navigation data, the navigation module 905 locates (or determines) the estimated state of the medical instrument within a tubular network. As shown in FIG. 9A, the navigation module 905 further includes various algorithm modules, such as an EM-based algorithm module 950, an image-based algorithm module 960, and a robot-based algorithm module 970, that each may consume mainly certain types of input data and contribute a different type of data to a state estimator 980. As illustrated in FIG. 9A, the different kinds of data output by these modules, labeled EM-based data, the image-based data, and the robot-based data, may be generally referred to as "intermediate data" for sake of explanation. The detailed composition of each algorithm module and of the state estimator 980 is more fully described in FIG. 9B below.

VI. B. Navigation Module

FIG. 9B shows an example block diagram of the navigation module 905 shown in FIG. 9A, according to one embodiment. As introduced above, the navigation module 905 further includes a state estimator 980 as well as multiple algorithm modules that employ different algorithms for navigating through a tubular network. For clarity of description, the state estimator 980 is described first, followed by the description of the various modules that exchange data with the state estimator 980.

VI. B. 1 State Estimator

The state estimator 980 included in the navigation module 905 receives various intermediate data and provides the estimated state of the instrument tip as a function of time, where the estimated state indicates the estimated location and orientation information of the instrument tip within the tubular network. The estimated state data are stored in the estimated data store 985 that is included in the state estimator 980.

FIG. 9C shows an example block diagram of the estimated state data store 985 included in the state estimator 980, according to one embodiment. The estimated state data store 985 may include a bifurcation data store 1086, a position data store 1087, a depth data store 1088, and an orientation data store 1089, however this particular breakdown of data storage is merely one example, and in alternative embodiments not shown, different and/or additional data stores can be included in the estimated state data store 985.

The various stores introduced above represent estimated state data in a variety of ways. Specifically, bifurcation data refers to the location of the medical instrument with respect to the set of branches (e.g., bifurcation, trifurcation or a division into more than three branches) within the tubular network. For example, the bifurcation data can be set of branch choices elected by the instrument as it traverses through the tubular network, based on a larger set of available branches as provided, for example, by the 3D model which maps the entirety of the tubular network. The bifurcation data can further include information in front of the location of the instrument tip, such as branches (bifurcations) that the instrument tip is near but has not yet traversed through, but which may have been detected, for example, based on the tip's current position information relative to the 3D model, or based on images captured of the upcoming bifurcations.

Position data indicates three-dimensional position of some part of the medical instrument within the tubular network or some part of the tubular network itself. Position data can be in the form of absolute locations or relative locations relative to, for example, the 3D model of the tubular network. As one example, position data can include the position of a specific branch.

Depth data indicates depth information of the instrument tip within the tubular network. Example depth data includes the total insertion (absolute) depth of the medical instrument into the patient as well as the (relative) depth within an identified branch. Depth data may be determined based on position data regarding both the tubular network and medical instrument.

Orientation data indicates orientation information of the instrument tip, and may include overall roll, pitch, and yaw in relation to the 3D model as well as pitch, roll, raw within an identified branch.

Turning back to FIG. 9B, the state estimator 980 provides the estimated state data back to the algorithm modules for generating more accurate intermediate data, which the state estimator uses to generate improved and/or updated estimated states, and so on forming a feedback loop. For example, as shown in FIG. 9B, the EM-based algorithm module 950 receives prior EM-based estimated state data (not shown in FIG. 9B), also referred to as data associated with timestamp "t−1." The state estimator 980 uses this data to generate "estimated state data (prior)" that is associated with timestamp "t−1," It then provides the data back to the EM-based algorithm module. The "estimated state data (prior)" may be based on a combination of different types of intermediate data (e.g., robotic data, image data) that is associated with timestamp "t−1" as generated and received from different algorithm modules. Next, the EM-based algorithm module 950 runs its algorithms using the estimated state data (prior) to output to the state estimator 980 improved and updated EM-based estimated state data, which is represented by "EM-based estimated state data (current)" here and associated with timestamp t. This process continues to repeat for future timestamps as well.

As the state estimator 980 may use several different kinds of intermediate data to arrive at its estimates of the state of the medical instrument within the tubular network, the state estimator 980 is configured to account for the various different kinds of errors and uncertainty in both measurement and analysis that each type of underlying data (robotic, EM, image) and each type of algorithm module might create or carry through into the intermediate data used for consideration in determining the estimated state. To address these, two concepts are discussed, that of a probability distribution and that of confidence value.

The "probability" of the "probability distribution", as used herein, refers to a likelihood of an estimation of a possible location and/or orientation of the medical instrument being correct. For example, different probabilities may be calculated by one of the algorithm modules indicating the relative likelihood that the medical instrument is in one of several different possible branches within the tubular network. In one embodiment, the type of probability distribution (e.g., discrete distribution or continuous distribution) is chosen to match features of an estimated state (e.g., type of the estimated state, for example continuous position information vs. discrete branch choice). As one example, estimated states for identifying which segment the medical instrument is in for a trifurcation may be represented by a discrete probability distribution, and may include three discrete values of 20%, 30% and 50% representing chance as being in the location inside each of the three branches as determined by one of the algorithm modules. As another example, the estimated state may include a roll angle of the medical instrument of 40±5 degrees and a segment depth of the instrument tip within a branch may be is 4±1 mm, each represented by a Gaussian distribution which is a type of continuous probability distribution. Different methods can be used to generate the probabilities, which will vary by algorithm module as more fully described below with reference to later figures.

In contrast, the "confidence value," as used herein, reflects a measure of confidence in the estimation of the state provided by one of the algorithms based one or more factors. For the EM-based algorithms, factors such as distortion to EM Field, inaccuracy in EM registration, shift or movement of the patient, and respiration of the patient may affect the confidence in estimation of the state. Particularly, the confidence value in estimation of the state provided by the EM-based algorithms may depend on the particular respiration cycle of the patient, movement of the patient or the EM field generators, and the location within the anatomy where the instrument tip locates. For the image-based algorithms, examples factors that may affect the confidence value in estimation of the state include illumination condition for the location within the anatomy where the images are captured, presence of fluid, tissue, or other obstructions against or in front of the optical sensor capturing the images, respiration of the patient, condition of the tubular network of the patient itself (e.g., lung) such as the general fluid inside the tubular network and occlusion of the tubular network, and specific operating techniques used in, e.g., navigating or image capturing.

For example one factor may be that a particular algorithm has differing levels of accuracy at different depths in a patient's lungs, such that relatively close to the airway opening, a particular algorithm may have a high confidence in its estimations of medical instrument location and orientation, but the further into the bottom of the lung the medical instrument travels that confidence value may drop. Generally, the confidence value is based on one or more systemic factors relating to the process by which a result is determined, whereas probability is a relative measure that arises when trying to determine the correct result from multiple possibilities with a single algorithm based on underlying data.

As one example, a mathematical equation for calculating results of an estimated state represented by a discrete probability distribution (e.g., branch/segment identification for a trifurcation with three values of an estimated state involved) can be as follows:

$$S_1 = C_{EM} * P_{1,EM} + C_{Image} * P_{1,Image} + C_{Robot} * P_{1,Robot};$$

$$S_2 = C_{EM} * P_{2,EM} + C_{Image} * P_{2,Image} + C_{Robot} * P_{2,Robot};$$

$$S_3 = C_{EM} * P_{3,EM} + C_{Image} * P_{3,Image} + C_{Robot} * P_{3,Robot}$$

In the example mathematical equation above, $S_i (i=1, 2, 3)$ represents possible example values of an estimated state in a case where 3 possible segments are identified or present in the 3D model, $C_{EM}$, $C_{Image}$, and $C_{Robot}$ represents confidence value corresponding to EM-based algorithm, image-based algorithm, and robot-based algorithm and $P_{i,EM}$, $P_{i,Image}$, and $P_{i,Robot}$ represent the probabilities for segment i.

To better illustrate the concepts of probability distributions and confidence value associated with estimate states, a detailed example is provided here. In this example, a user is trying to identify segment where a instrument tip is located in a certain trifurcation within a central airway (the predicted region) of the tubular network, and three algorithms modules are used including EM-based algorithm, image-based algorithm, and robot-based algorithm. In this example, a probability distribution corresponding to the EM-based algorithm may be 20% in the first branch, 30% in the second branch, and 50% in the third (last) branch, and the confidence value applied to this EM-based algorithm and the central airway is 80%. For the same example, a probability distribution corresponding to the image-based algorithm may be 40%, 20%, 40% for the first, second, and third branch, and the confidence value applied to this image-based algorithm is 30%; while a probability distribution corresponding to the robot-based algorithm may be 10%, 60%, 30% for the first, second, and third branch, and the confidence value applied to this image-based algorithm is 20%. The difference of confidence values applied to the EM-based algorithm and the image-based algorithm indicates that the EM-based algorithm may be a better choice for segment identification in the central airway, compared with the image-based algorithm. An example mathematical calculation of a final estimated state can be:

for the first branch: 20%*80%+40%*30%+10%*20%=30%; for the second branch: 30%*80%+20%*30%+60%*20%=42%; and for the third branch: 50%*80%+40%*30%+30%*20%=58%.

In this example, the output estimated state for the instrument tip can be the result values (e.g., the resulting 30%, 42% and 58%), or derivative value from these result values such as the determination that the instrument tip is in the third branch.

As above the estimated state may be represented in a number of different ways. For example, the estimated state may further include an absolute depth from airway to location of the tip of the instrument, as well as a set of data representing the set of branches traversed by the instrument within the tubular network, the set being a subset of the entire set of branches provided by the 3D model of the patient's lungs, for example. The application of probability distribution and confidence value on estimated states allows improved accuracy of estimation of location and/or orientation of the instrument itp within the tubular network.

VI. B. 2 Algorithm Modules

A shown in FIG. 9B, the algorithm modules include an EM-based algorithm module 950, an image-based algorithm module 960, and a robot-based algorithm module 970. The algorithm modules shown in FIG. 9B is merely one example, and in alternative embodiments, different and/ additional algorithm modules involving different and/or additional navigation algorithms can also be included in the navigation module 905.

VI. B. 2. I. EM-Based Algorithm Module

Figure 10A:
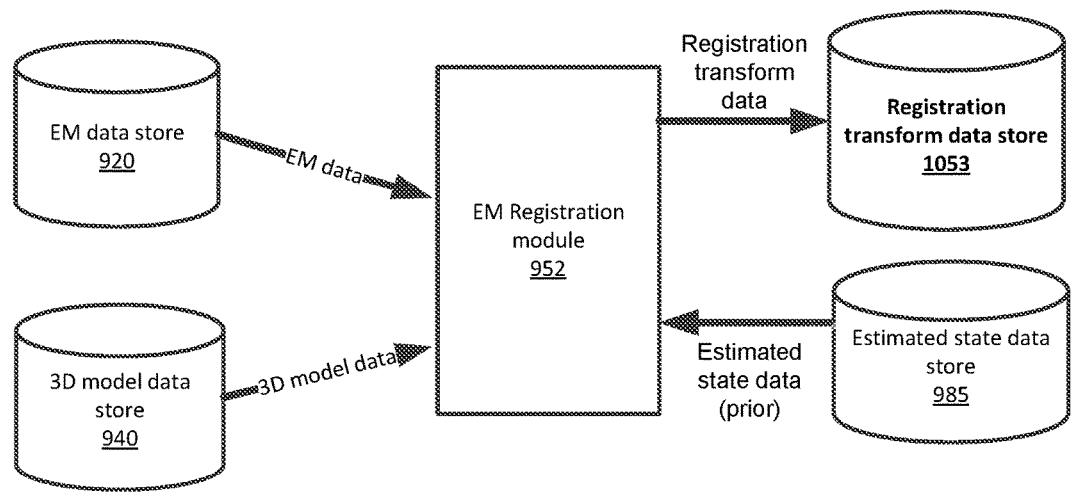
FIG. 10A shows an example block diagram of the EM registration module, according to one embodiment.

The EM-based algorithm module 950 further includes an EM registration module 952 and a branch selection module 954. The EM registration module 952 performs registration of EM coordinates to 3D model coordinates. FIG. 10A shows an example block diagram of the EM registration module 952, according to one embodiment. The EM registration module 952 receives as input, estimated state data (prior) (e.g., bifurcation data) from the estimated state data store 1086, the EM data from the EM data store 920, the 3D model data from the 3D model data store 940.

As described above with respect to Section V, based on the received data, the EM registration module 952 performs on-the-fly registration of the EM tracking data to the 3D model. After the initial registration is determined, the EM registration module 952 continually updates its estimate of the registration transform based on received data, so as to increase transform accuracy as well as to compensate for changes to the navigation configuration system 900, e.g., changes due to movement of the patient. The EM registration module 952 outputs registration transform data to the registration transform data store 1053. In one embodiment, the registration transform data reflects the best fit registration transform, and it can also be sent to the state estimator 980, as well as to the branch selection module 954.

Figure 10B:
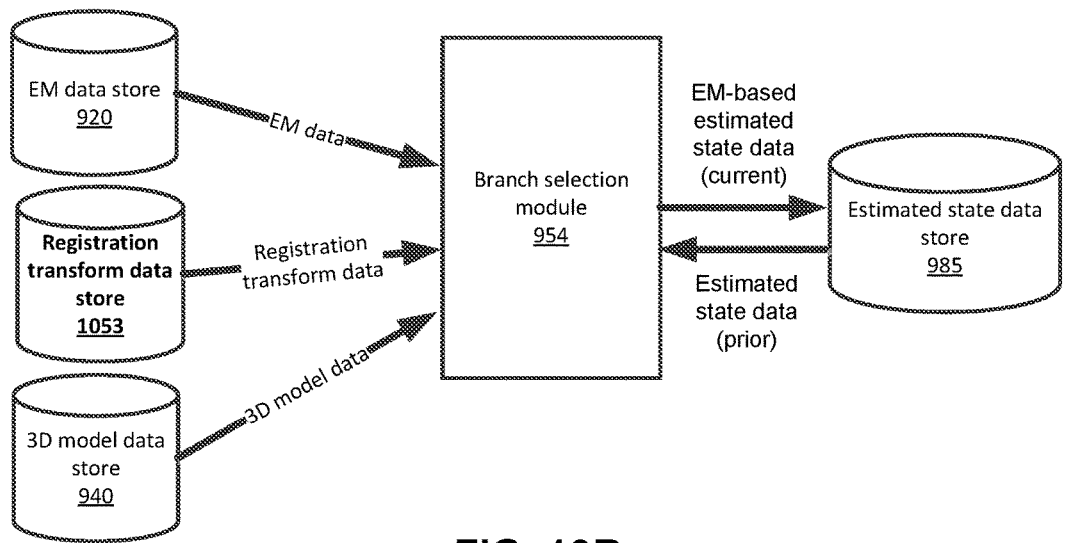
FIG. 10B shows an example block diagram of the branch selection module, according to one embodiment.

FIG. 10B shows an example block diagram of the branch selection module 954, according to one embodiment. The branch selection module 954 receives as inputs, estimated state data (prior) (e.g., bifurcation data) from the estimated state data store 985, the EM data from the EM data store 920, registration transform data from the registration transform data store 1053, as well as 3D model data from the 3D model data store 940. Based on the received data, the branch selection module 954 determines an estimate of the position and orientation of the endoscope tip relative to the 3D model of the tubular network and provides EM-based estimated state data (current) to the state estimator 980. As an example, the EM-based estimated state data may be represented as a probability distribution (e.g., a discrete distribution of 20%, 30% and 50% for three segments of a trifurcation, as described above.) Additionally, when at a bifurcation as indicated by the received bifurcation data, the branch selection module 954 may compare the pitch and yaw of the tip to the angles of each branch in the 3D model to estimate which branch has been selected by the user for traversal. The branch selection module 954 outputs the EM-based estimated state data (current) to the estimated data store 985.

VI. B. 2. II. Image-Based Algorithm Module

Turning back to FIG. 9B, the image-based algorithm module 960 uses image data to determine the estimated state of the instrument within the tubular network. The image-based algorithm module 960 further includes one or more different types of image-based algorithm modules that employ different image-based algorithms. As shown in FIG. 9B, one example including an object-based algorithm module 962 is shown. In alternative embodiments not shown, other types of image-based algorithms may be employed and corresponding algorithm modules may be included in the image-based algorithm module 960.

The object-based algorithm module 962 detects and analyzes objects present in the field of view of the image data, such as branch openings or particles, to determine estimated state. In one embodiment, it includes an object detection module 963, and object mapping module 964, a topological reasoning module 965, and a motion estimation module 966. In some embodiments, it may or may not be necessary to apply the different modules 963, 964, 965 and 966 in a fixed sequential order, and when actually executing a process of object-based algorithm described by the object-based algorithm module 962, the order of employing each module within the module 962 is a different order than shown in FIG. 9B.

Figure 10C:
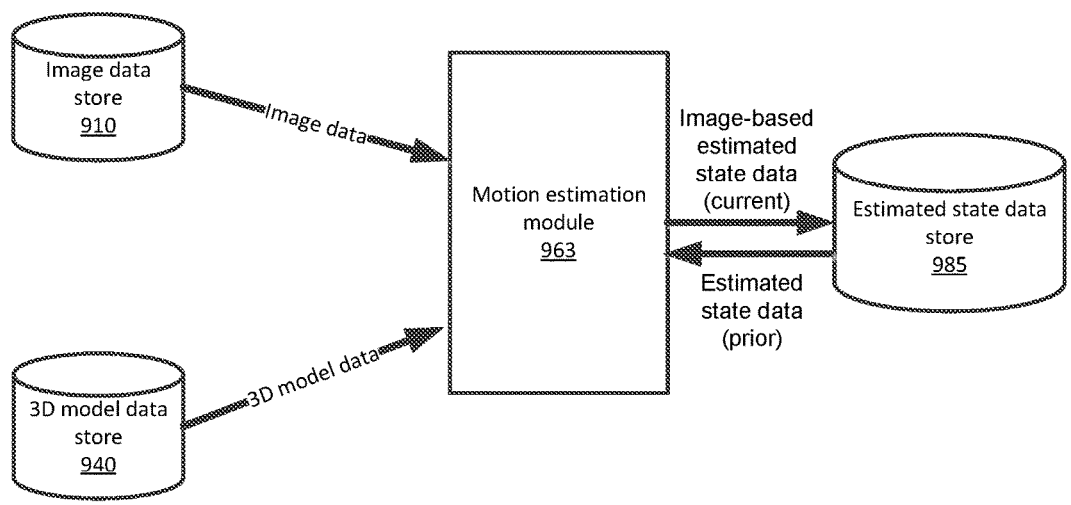
FIG. 10C shows an example block diagram of the motion estimation module, according to one embodiment.

Turning to FIG. 10C, the motion estimation module 963 receives as inputs image data from the image data store 910, estimated state data (prior) (specifically bifurcation data), from the estimated state data store 985 as well as the 3D model data from the 3D model data store 940. Based on the received image data, the motion estimation module 963 measures a movement of the medical instrument between multiple image frames based on the received image data. Example techniques used include optical flow and image registration techniques, among others. This measurement determines a differential movement, such as forward-backward motion or roll motion, of the instrument tip in its own local frame of reference. This movement can be combined with the prior estimated state input to calculate a new estimated state. In particular, a forward (or backward) movement can translate into an increase (or decrease) in depth relative to a prior estimated state. Similarly, a differential roll translates into a change in roll angle relative to a prior estimated state. These measurements allow an estimation of movement through the tubular network. As above, these estimations may be represented as a probability distribution (e.g., a roll angle of the medical instrument of 40±5 degrees represented by a Gaussian distribution). The output estimated state is stored in the estimated state data store 985.

In one embodiment, in a case where the estimated state and bifurcation data for a particular instant in time indicate that the instrument tip is at or near a branch point, this movement measurement may include an identification of an estimated new branch that the instrument tip is estimated to be entering or have entered. For example, if the bifurcation data indicates that the endoscope tip is at a branch point, pitch and yaw movements can be measured to determine changes in pointing angle, and the new estimated angle can be compared with the expected angles of different branches in the 3D model of the tubular network. A determination can then be made of which branch the endoscope is facing towards when it is moved into a new branch. Estimated state data reflecting each of these estimates of new position, orientation, and/or branch entry are output to the state estimator 980.

Figure 10D:
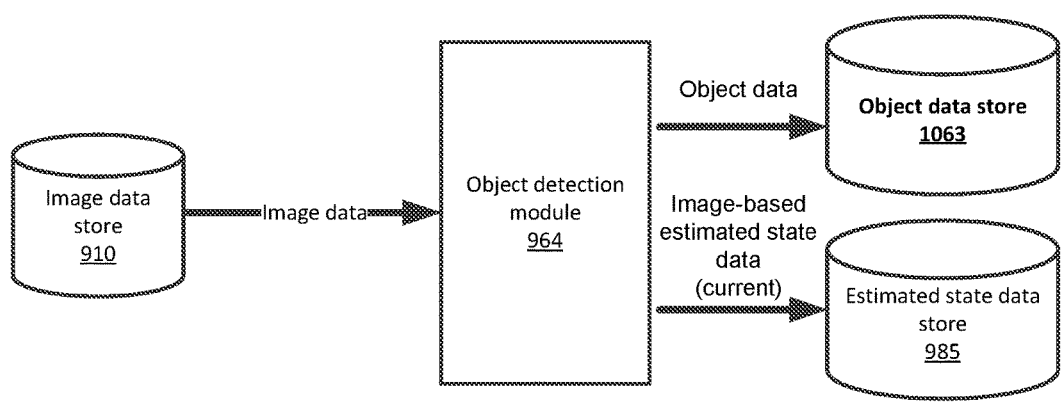
FIG. 10D shows an example block diagram of the object detection module, according to one example.

FIG. 10D shows an example block diagram of the object detection module 964, according to one example. The object detection module 964 receives as inputs image data (e.g., image frames), and outputs object data to an object data store 1063 as well as estimated state data to the estimated state data store 985. Object data indicates information about what objects were identified, as well as positions, orientations, and sizes of objects represented as probabilities.

Specifically, the object detection module 964 detects, within an image, one or more objects and one or more features of the object(s) that may indicate branch points in a tubular network, and then determines their position, size, and orientation. Objects may be calculated or represented in the object detection module 964 as being two-dimensional shapes, such as circles/ovals/ellipses for detected branch points. This corresponds to the fact that the image data used to capture the objects are images from the camera on the instrument tip pointed usually along an axis substantially parallel to the direction of the segment in which the instrument is located. As a consequence, objects such as branches in the tubular network appear as simple shapes such as ellipses in the images. In one embodiment, in a given image within a tubular network, each branch will typically appear as a dark, approximately elliptical region, and these regions may be detected automatically by a processor, using region-detection algorithms such as maximally stable extremal regions (MSER) as objects. These regions may then be fit to define an object (e.g., ellipse), with appropriate free parameters such as ellipse center, major and minor axes, and angle within the image. The roll measurement and the identified matching between model lumens and lumens in the image are also output to the state estimator 980, as well as topological reasoning module 966. An example of identified objects superimposed on an image of a bronchial network, along with a link joining their centers, is described with reference to FIGS. 11A-11B.

In one embodiment, "airway" can also be identified as an object present in the image data. The object detection module 964 may use light reflective intensity combined with other techniques to identify airways.

The object detection module 964 may further track detected objects across a set of sequential image frames to detect which branch has been entered from among a set of possible branches in the tubular network. Tracking the relative positions of the objects within the image frames may be used to determine a local, absolute measurement of roll angle within a branched network.

Figure 10E:
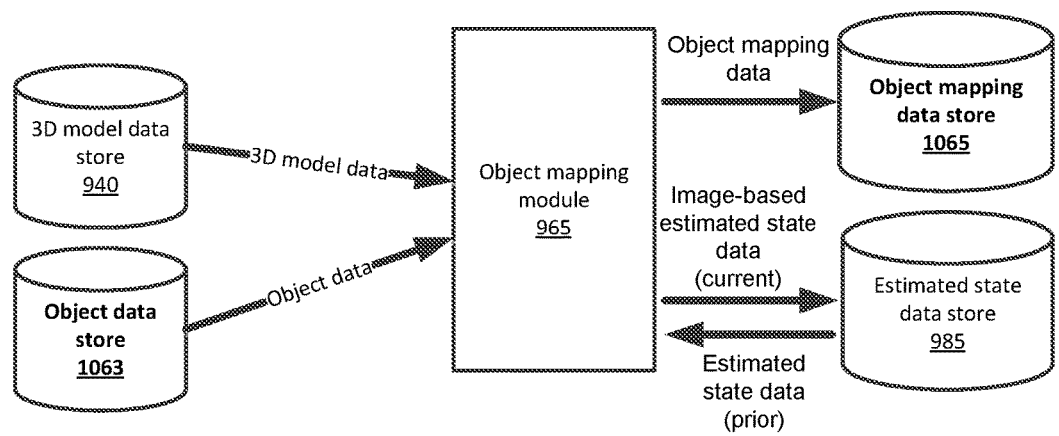
FIG. 10E shows an example block diagram of the object mapping module, according to one embodiment.

FIG. 10E shows an example block diagram of the object mapping module 965, according to one embodiment. The object mapping module 965 receives as inputs 3D model data from the 3D model data store 940, object data (e.g., detected objects such as shapes representing possible branches in the tubular network) from the object data store 1063, and estimated state data (prior) from the estimated state data store 985.

Based on the received input data, the object mapping module 965 outputs object mapping data to an object mapping data store 1065 as well as image-based estimated state data (current) to the estimated state data store 985. As one example, the object mapping data indicates mapping information between physical branches (lumens) shown in image data (based on the detected objects) and virtual branch information generated by 3D model. The estimated state data (current) generated by module 965 includes identification of each branch of the tubular network visible within the image as well as an estimate of the roll of the endoscope tip relative to the 3D model. As above, the estimated state data (current) can be represented as a probability distribution. The identification of the visible lumens may include coordinates in x and y of each identified lumen center within the image, for example based on object sizes correlated with the 3D model virtual image data, as well as an association of each identified lumen location with a particular branch of the tubular network.

In some embodiments, since the 3D model is generated prior to the endoscopic procedure, the virtual images of the tubular network may be pre-computed to speed up processing. In alternative embodiments not shown, the tubular network may be represented by a structure such as a tree diagram of lumen midlines, with each such midline describing a 3D path, so that an expected position of local branch centers as seen from any arbitrary perspective may be compared to the identified actual locations of branch centers based on EM data and/or robot data.

Figure 11A:
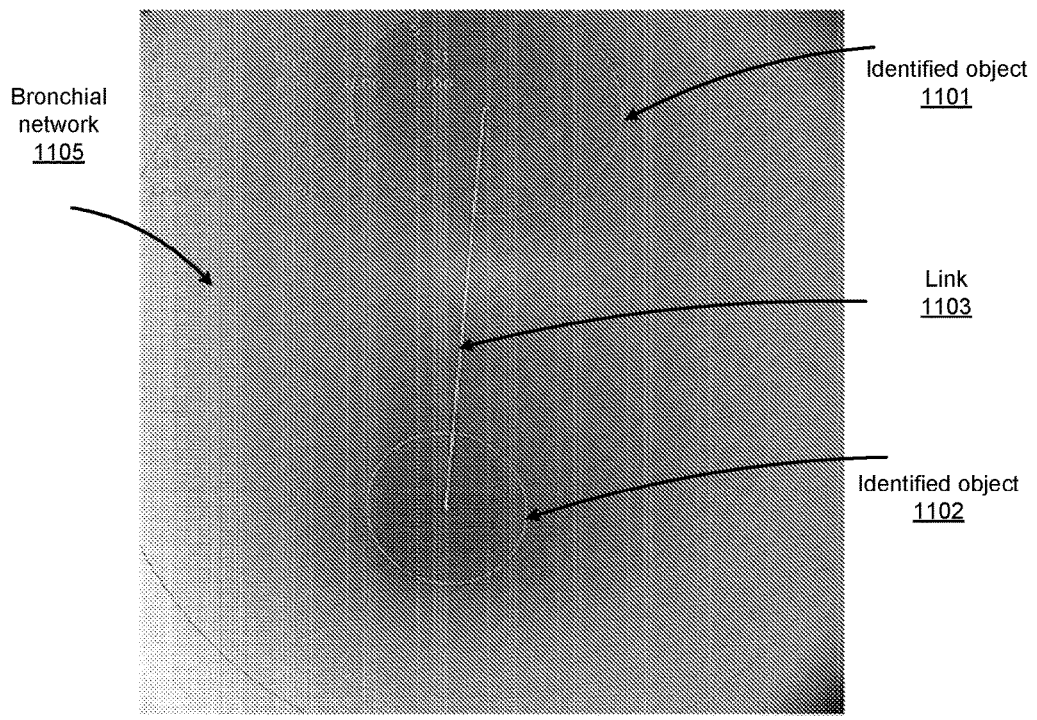
FIG. 11A shows two example identified objects superimposed on an image of a bronchial network along with a link connecting centers of the two objects, according to one embodiment.
Figure 11B:
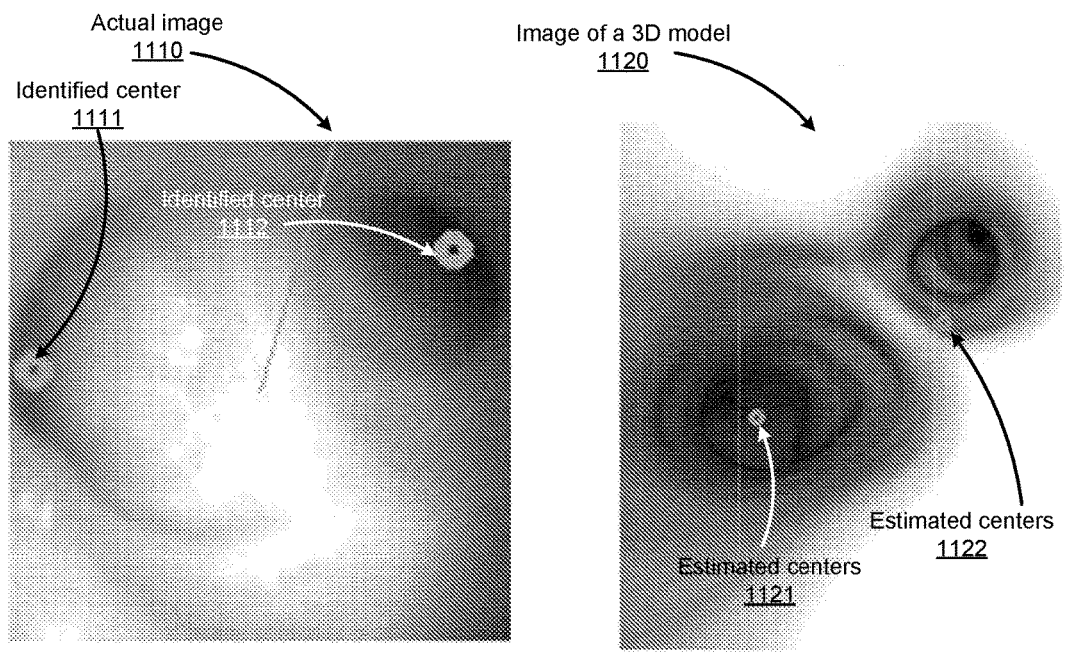
FIG. 11B shows a matching between airway lumens in an actual image of a real bronchial network and a 3D model of the network, according to on embodiment.

FIGS. 11A-11B, show an example object-to-lumen mapping performed by the object mapping module 965, according to one embodiment. More specifically, FIG. 11A shows two example identified objects 1101 and 1102 superimposed on an image of a bronchial network 1105 along with a link 1103 connecting centers of the two objects, according to one embodiment. In the illustrated example, the identified objects 1101 and 1102 are ellipse-shaped.

FIG. 11B shows a matching between airway lumens in an actual image 1110 of a real bronchial network and a corresponding virtual image 1120 from a 3D model of that same network, according to on embodiment. In the actual image 1110, ellipses are identified corresponding to two different branches, located with identified centers 1111 and 1112, which, in one embodiment, indicates centerline coordinates of the branches as described above in FIGS. 6A-6B. The 3D model virtual image 1120 is a simulated representation of the real bronchial network shown in the actual image 1110, and the estimated centers 1121 and 1122 of the endoscope tip as determined by the state estimator 980 are shown corresponding to the positions of the identified centers 1111 and 1112.

If both images 1110 and 1120 are presented to a user via a user interface, the 3D model image 1120 may be rotated or translated to increase the closeness of fit between actual image 1110 and virtual image 1120, and the amount of roll needed for the rotation or translation can be output as a correction to the current estimated state (e.g., roll of the instrument tip).

In one embodiment, the probability applied to a possible estimated state as generated by the object mapping module 965 is based on the closeness of fit between the identified centers 1111 and 1112 detected in the actual image 1110 and estimated centers 1121 and 1121 in the 3D model image 1120, and as one example, the probability of being in the lumen with identified center 1112 drops as the distance between the estimated center 1122 and identified center 1112 increases.

Figure 10F:
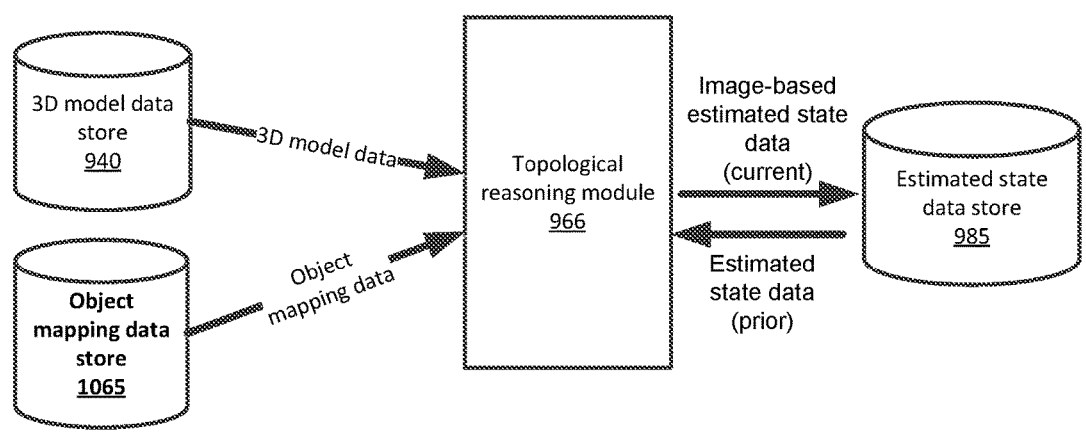
FIG. 10F shows an example block diagram of the topological reasoning module, according to one embodiment.

FIG. 10F shows an example block diagram of the topological reasoning module 966, according to one embodiment. The topological reasoning module 966 receives as input image data from the 3D model data from the 3D model data store 940, object mapping data from the object mapping data store 1065, and estimated state data (prior) from the estimated state data store 985.

Based on the received data, the topological reasoning module 966 determines which branch the endoscope tip is facing towards, thereby generating a prediction of which branch will be entered if the endoscope is moved forward. As above, the determination may be represented as a probability distribution. In one embodiment, when the instrument tip is moving forward, the topological reasoning module 966 determines that a new branch of the tubular network has been entered and identifies which branch the tip has moved into. The determination of which branch is being faced and which segment is entered may be made, for example, by comparing the relative sizes and locations of different identified objects (e.g., ellipses). As one example, as a particular lumen branch is entered, a corresponding detected object will grow larger in successive image frames, and will also become more centered in those frames. If this is behavior is identified for one of the objects, the topological reasoning module 966 assigns an increasingly large probability to a corresponding estimated state as the endoscope tip moves towards the lumen associated with that object. Other branches are assigned correspondingly lower probabilities, until finally their object shapes disappear from images entirely. In one embodiment, the probability of the medical instrument being in those branches depends only on the probability that the branches were misidentified by the object mapping module 964. The output of the topological reasoning module 966 is image-based estimated state data representing estimated probabilities of being in each of a set of possible branches within the branched network.

VI. B. 2. III. Robot-Based Algorithm Module

The robot-based algorithm module 970 uses robot data to provide robot-based estimated state data to the state estimator 980. FIG. 9B illustrates that the robot-based algorithm module 970 receives estimated state data (prior) and provides estimated state data (current) to state estimator 980. Robot data includes data related to physical movement of the medical instrument or part of the medical instrument (e.g., the instrument tip) within the tubular network. Example robot data includes command data instructing the instrument tip to reach a specific anatomical site and/or change its orientation (e.g., with a specific pitch, roll, yaw, insertion, and retraction for one or both of a leader and a sheath) within the tubular network, insertion data representing insertion movement of the part of the medical instrument (e.g., the instrument tip or sheath), IDM data, and mechanical data representing mechanical movement of an elongate member of the medical instrument, for example motion of one or more pull wires, tendons or shafts of the endoscope that drive the actual movement of the medical instrument within the tubular network.

Although in an ideal system, specifically input pitch, roll, yaw, insertion, and retraction commands given to the IDM to control the instrument tip would result in exactly-as-input changes in the motion of the instrument tip, in practice this is generally not the case. Friction in the system, nonlinearities in instrument motion, blockages, and other effects may cause the input motion to vary from the output motion. As such, the estimated state data provided by the raw robotic input data is just that, an estimate as to actual motion. As per the algorithms above, the estimated state data determined from the robotic data may be represented in a probabilistic manner to represent this uncertainty in actual position information.

VI. C. Probability Distribution Generation

Figure 12:
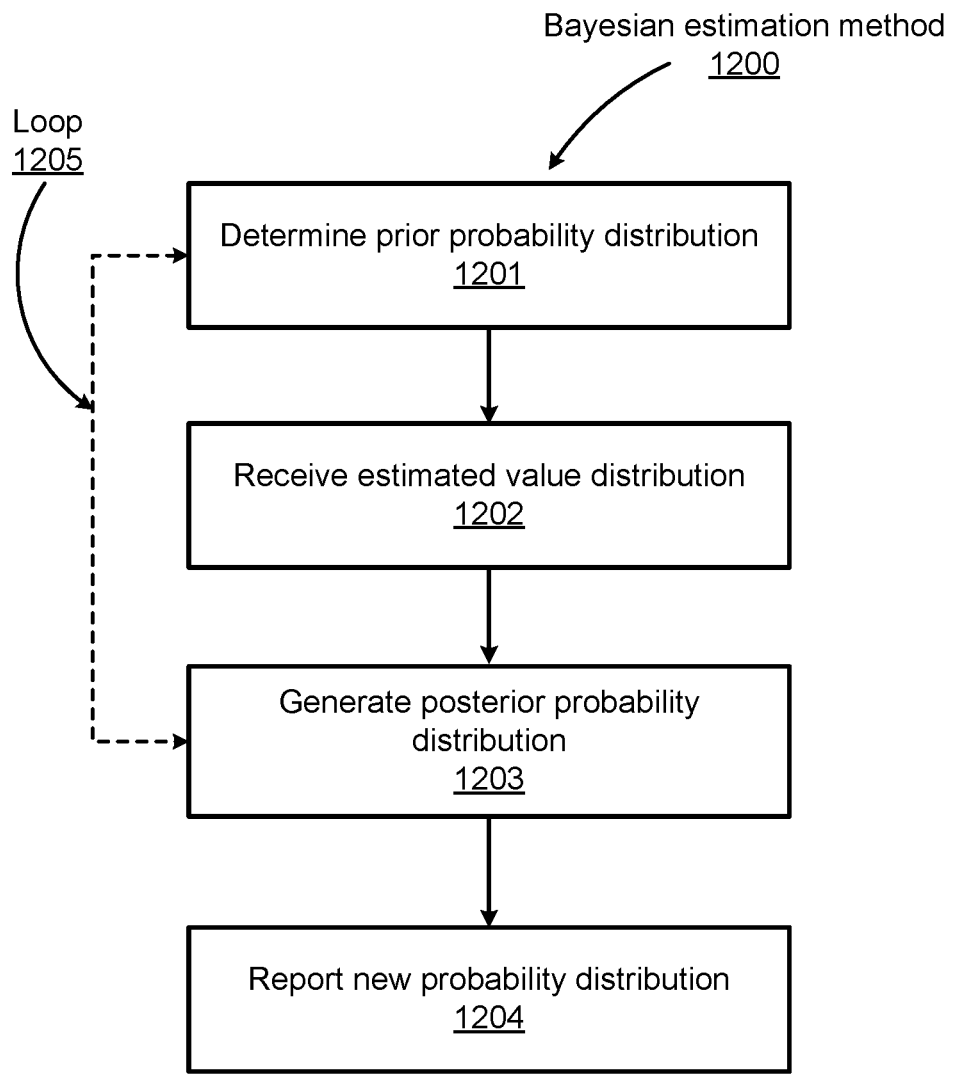
FIG. 12 shows an example process of generating a probability distribution over multiple values of an estimated state by the state estimator, according to one embodiment.

FIG. 12 shows an example process of generating a probability distribution over multiple values to determine an estimated state as may be performed by any of the individual algorithm modules described above, according to one embodiment. For sake of example, this process is described with respect to the estimated state module 980, but in practice may be used by any algorithm module.

In FIG. 12, a process of a Bayesian estimation method is shown, and in alternative embodiments not shown, other methods of generating a probability distribution can also be employed. As shown in FIG. 12, the state estimator 980 first determines 1201 a prior probability distribution for the estimated state. As this stage, this probability distribution may be an initialized value distribution based, for example, on user input identifying a starting point near an entry point to a branched network. Subsequently, the distribution is determined from its previous output state estimate, adjusted based on the robotic, image, or EM input data.

For example, if the surgical robotic system 100 commands to move the endoscope tip forward a certain distance, e.g., 1 mm, the new or updated probability distribution may be estimated as centered 1 mm forward compared to the previous probability distribution. More generally, if a robot command is expected to change a variable x by a certain amount, represented by an expected distribution of value changes $Q(\Delta x)$, the new estimated distribution $P'(x)$ may be expressed as a convolution of the previous distribution $P(x)$ with $Q(\Delta x)$. This new estimated state is treated as a prior probability estimate of the variable for the subsequent steps.

In the next step 1202, the state estimator 980 receives an estimated value distribution for the estimated state based on one or more algorithm modules. This value distribution may be represented in various ways, such as an expected value and an error range, or as an explicit distribution function over values, for example. In any case, the value distribution contains, implicitly or explicitly, an expected value of the variable and some estimate of a range of error. In some cases, only the expected value is transmitted and the error range is determined by the state estimator 980, using a record of past performance or pre-calibrated values of reliability. In one embodiment, when using an expected value and an error range, the state estimator 980 may treat the estimated value distribution as a normal distribution with a mean at the expected value and a standard deviation determined by the error range. In the case of a discrete variable or discrete state like branch identification, the estimated value distribution will typically comprise one or more probability values assigned to each of one or more branches, such that the total probability sums to one (or 100%). In some cases, some branches may not be assigned with explicit probabilities, and the total probability may be less than 1, in which case the remaining probability can be treated as being uniformly distributed over all other branches.

In step 1203, the state estimator 980 generates a posterior probability distribution based on the received estimated value distribution from step 1202 and the determined prior probability distribution from step 1201. As one example, this posterior probability distribution is calculated as an application of Bayes' Theorem, which states that for an observation A, the posterior probability $P(x|A)$ of a variable having value x is given by the equation $$P(x|A) = \frac{P(A|x)P(x)}{P(A)},$$

where $P(x|A)$ is the probability of observing A given that x is true, $P(x)$ is the prior probability of x being true, and $P(A)$ is the prior probability of observing A, whether x is true or false.

The state estimator 980 determines each of the quantities P(x), P(A), and P(A|x) from the inputs generated during steps 1201 and 1202, as well as from a basic model of the set of possible observations. For example, P(A), representing the prior probability of x, may simply be read from the value determined in step 1201. Likewise, P(A|x) may be read from the function determined in step 1202. P(A), may be set as a constant representing the number of possible values of A. For example, when estimating a discrete probability distribution for what branch an endoscope tip is in encountering a division into a certain number (e.g., 10) of branches, the probability, P(A), of observing the tip to be in any given branch, may be set as ⅒. Alternatively, a model may be implemented to weight the possible observations A variably, for example, where branch sizes vary, P(A) may be set proportional to the size of branch A divided by the sum of all branch sizes, representing the idea that a randomly-placed tip is more likely to be found in a large branch than a small one. For continuous distributions, such as roll angle, depth, or orientation, P(A) will be a probability density function over all possible observations A. For example, if roll angle ranges from 0 to $2\pi$ radians, P(A) may be set to $1/(2\pi)$ for all values of A to represent an equally likely probability density of any roll angle being observed. More generally, given P(x) as an estimate for the probability of x, P(A) will be given by the formula P(A)=P(A|x)P(x)+P(A|~x)P(~x), where ~x means "not-x."

In one embodiment, the result of step 1203 is a new probability distribution for values of the variable/state. In one embodiment, when each of multiple independent measurements relates to a given variable, the multiple independent measurements may be adjusted sequentially by taking the output of step 1203 as an input to step 1201, and using each new measurement as the estimated value distribution of step 1202. This generates a loop 1205 over measurements. Alternatively, step 1202 may incorporate a plurality of independent estimated value distribution which may be combined into a single updated estimate in step 1203, using Bayesian conditional updating on multiple measurements.

For example, if differential movement is being measured, the motion estimation module 963 may employ method 1200 with a process of taking the prior probability distribution of step 1201 as over an amount of movement (for example, an expected range of movement based on robot data), receiving an estimated value distribution in step 1202 over differential movement measurements, and generating a posterior probability distribution in step 1203 to estimate actual values of movement. This output may then be convolved with a prior estimated variable values (from a prior estimated state) to generate a posterior probability distribution for multiple values of the state. In some embodiments, once all measurements have been incorporated into an updated probability distribution, this new probability distribution is reported out in step 1204. The process 1200 may be applied in parallel to generate new probability distributions for a plurality of variables (states), such as position, orientation, roll, depth, and/or branch. The outputs of step 1204 for each such process may be combined together to generate a new estimated state (E) 1202, which represents the output of the motion estimation module 963.

VI. D. Error Correction

In some embodiments, the navigation module 905 allows estimates of variables even when certain input data is not available. For example, prior to registration of the EM system, the output of the branch selection module 954 is ignored by the state estimator 980. Nonetheless, states representing location and/or orientation (e.g., tip insertion depth) may still be estimated based on available input data like the robot input data. Each time the instrument tip is ordered to move deeper into the branched network, the estimate state for the tip insertion depth may be updated based on this estimated movement. Thus, prior to registration, the tip insertion depth may be estimated based on robot data, and after registration, the depth may be estimated based on data from the branch selection module 954, but also partially based on robot data, with a weighting function.

There is a possibility of over-determination/over-fitting of the location estimate for the instrument based on the many possible independent measurements introduced above, which include local measurements such as object-based image tracking, optical flow, global measurements such as EM tracking, and robotic input data based measurement. Consequently, the accuracy of estimated position within the branched network may be greater than the accuracy of estimates made using any one of the modules alone. Furthermore, in some embodiments, the navigation configuration system 900 demonstrates the ability to recover from errors by using the measurements from one module to contradict the measurements from another, allowing the system to "change its mind" about a previously-made determination. An example of how an error can be corrected is more fully described below with reference to FIG. 13.

Figure 13:
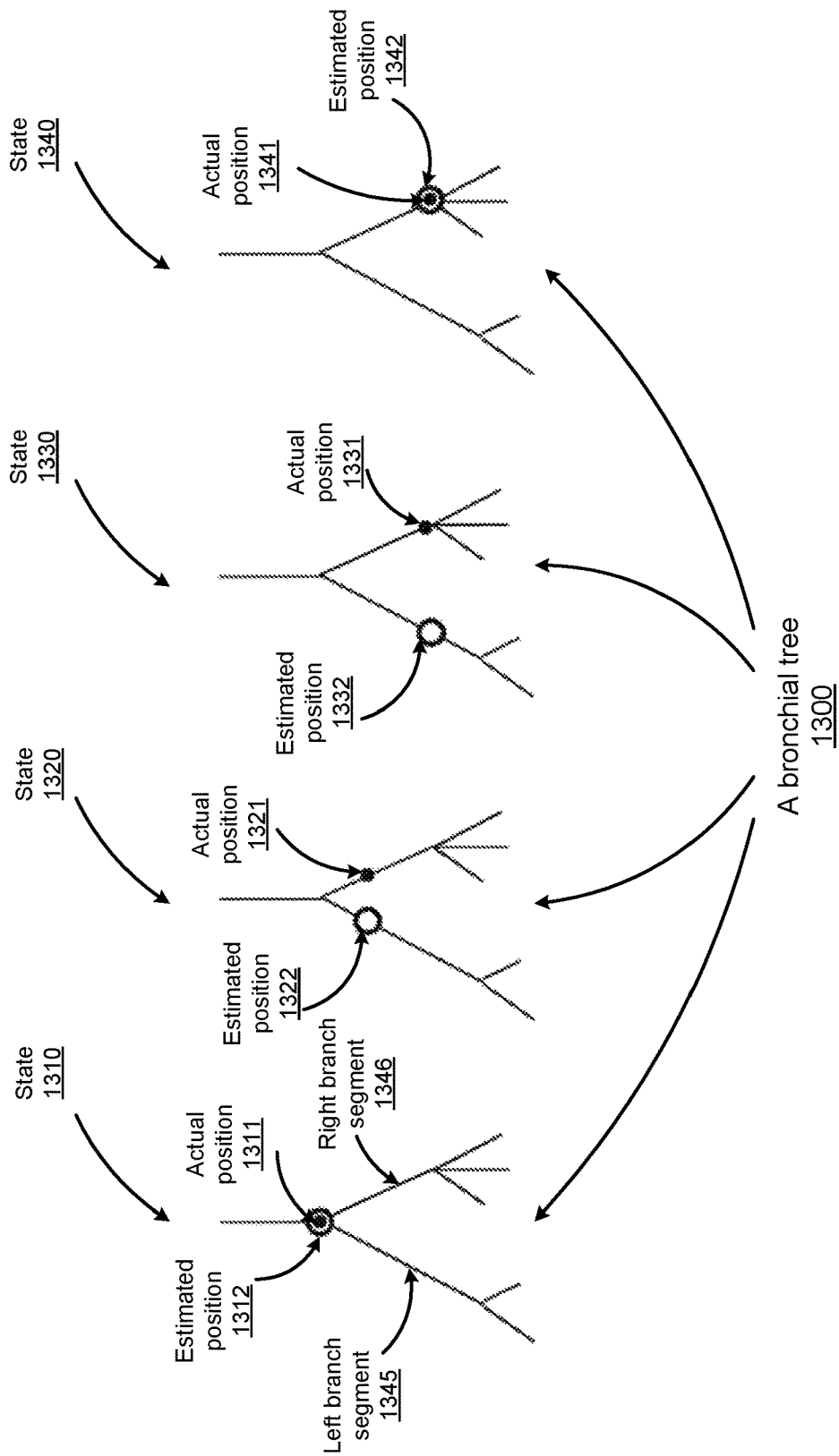
FIG. 13 shows an example of how an error can be corrected with navigation through a tubular network of bronchial tubes by the navigation configuration system, according to one embodiment.

FIG. 13 shows an example of how an error can be corrected with navigation through a tubular network by the navigation configuration system 900, according to one embodiment. In FIG. 13, a simplified model of a bronchial tree 1300 with estimated states is shown at four different temporal stages: states 1310, 1320, 1330, and 1340. For each temporal stage, an estimated position (1312, 1322, 1332, and 1342, respectively) of an instrument tip used for the navigation is illustrated, and a corresponding actual position (1311, 1321, 1331, and 1341, respectively) of the tip is also illustrated. In one embodiment, over time during the four stages, the accuracy of the estimated states (based on the underlying probabilities and confidences) may vary, e.g., the estimated states may first begin accurate, then becomes inaccurate, and then becomes accurate again.

As shown in FIG. 13, initially, in state 1310, the actual position of the tip is 1311, at the upper branch of the bronchial tree 1300, and the navigation configuration system 900 accurately estimates that location as estimated position 1312. However, when it enters one of the two branches near actual position 1311, one or more modules inside the system 900 may misidentify the branch based on probabilities provided by one or more of the algorithm modules, causing the system to conclude that the tip is entering the left branch 1345, when it is actually entering the right branch 1346. For example, the state estimator 980 initially assigns an 80% chance of being in the left branch and a 20% chance of being in the right branch.

However, as the endoscope tip proceeds down the right branch 1346 to state 1320, the estimated position 1322 will be more and more spatially distinct from the actual position 1321. In one embodiment, the branch selection module 954 may thus more and more confidently report that the tip is probably in the right branch 1346 based on the shift in the probabilities provided by the underlying modules. Accordingly, the state estimator's 980 aggregate probability estimate may also shift, thereby resulting in an increase in the probability of being in the right branch 1346 and a corresponding decreasing the probability of being in the left branch 1345.

The system 900 may proceed to a state 1330, in which the tip is at the actual position 1331, arriving at a division into three branches. However, at this point in time state estimator 980 may still be estimating that the most likely state to be at estimated position 1332.

At state 1340, based on the 3D model, the state estimator 980 may be expecting a certain distance until the next branch division, in this example a two-way division, rather than three-way branch division. Under this circumstance, both the branch selection module 954 and the object mapping module 964 may strongly estimate that the tip is located in the branch shown on the right, which further strongly adjusts the probabilities of being in the left and right branches, leading to an almost certain assignment of the tip location to the correct branch, the right branch 1346 here.

Consequently, at state 1340 the state estimator 980 correctly estimates the instrument tip be at estimated position 1342, very close to its actual location 1341. If the endoscope is along the user's desired path, the system 900 can now proceed to determine which branch of the three-way branch division is entered next. Alternately, the user can backtrack to travel down the left lumen of bronchial tree 1300. In some embodiments, this updated estimate is shown to a user on a display, so that the user can perceive that the previous estimates were in error, and that error has now been corrected.

VII. Pre-Operative Path Planning for Navigation Preparation

Figure 14A:
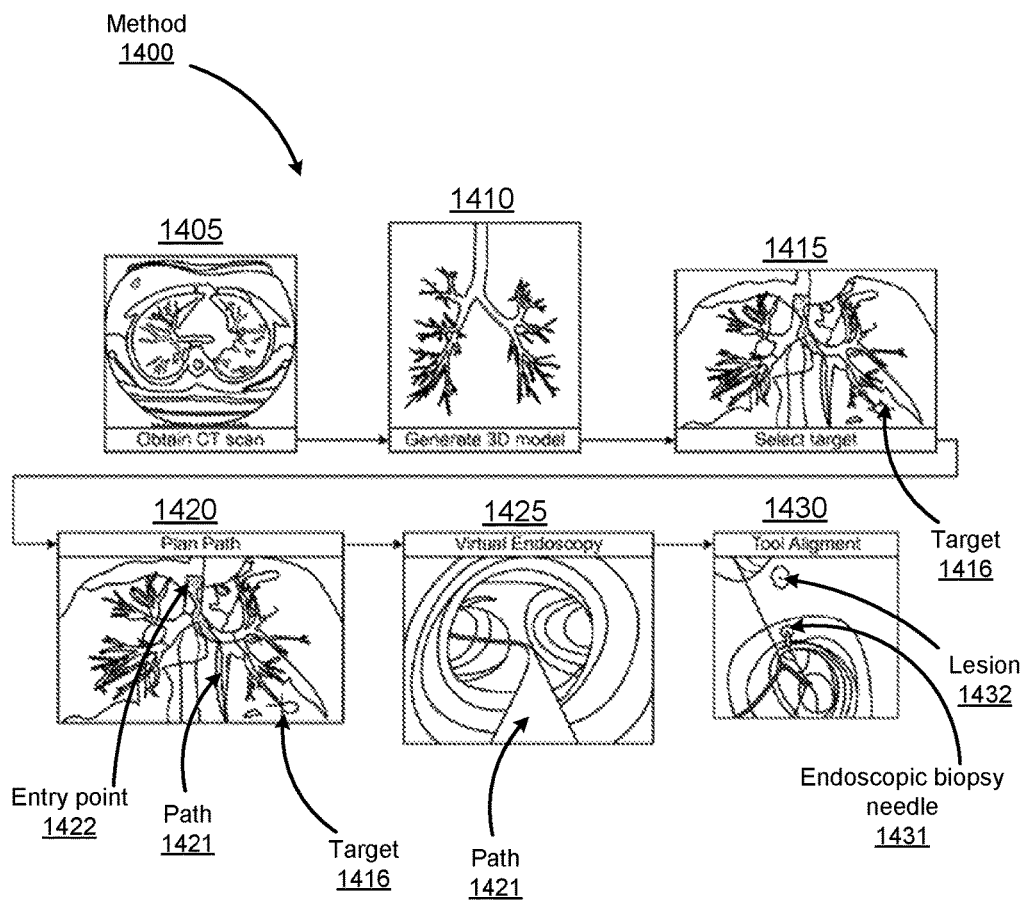
FIG. 14A shows an example pre-operative sequence of steps of a method for navigating the instrument tip to a particular site within the tubular network, according to one embodiment.
Figure 14B:
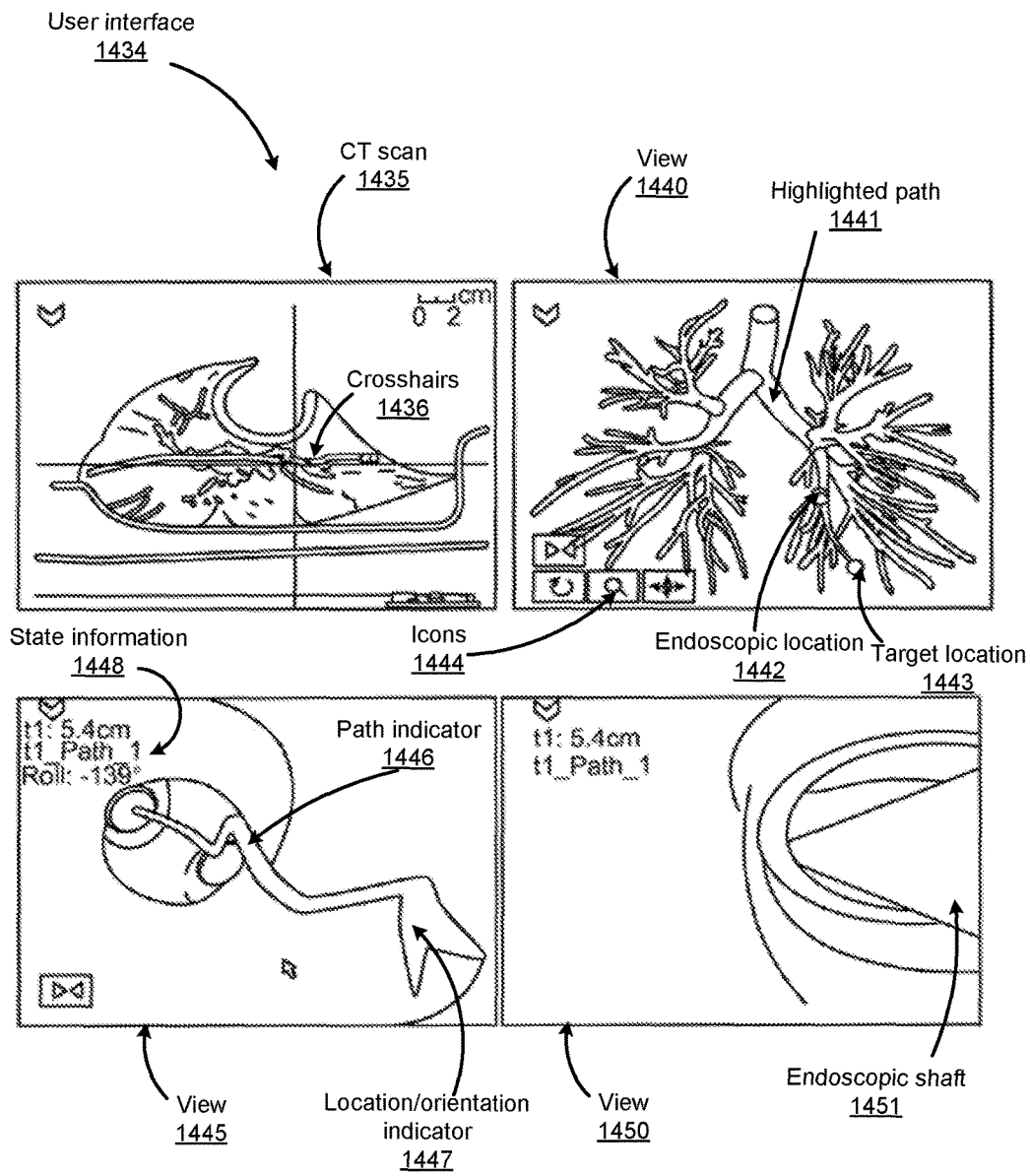
FIG. 14B shows an example user interface for navigation of a surgical instrument through a tubular network, according to one embodiment.
Figure 14C:
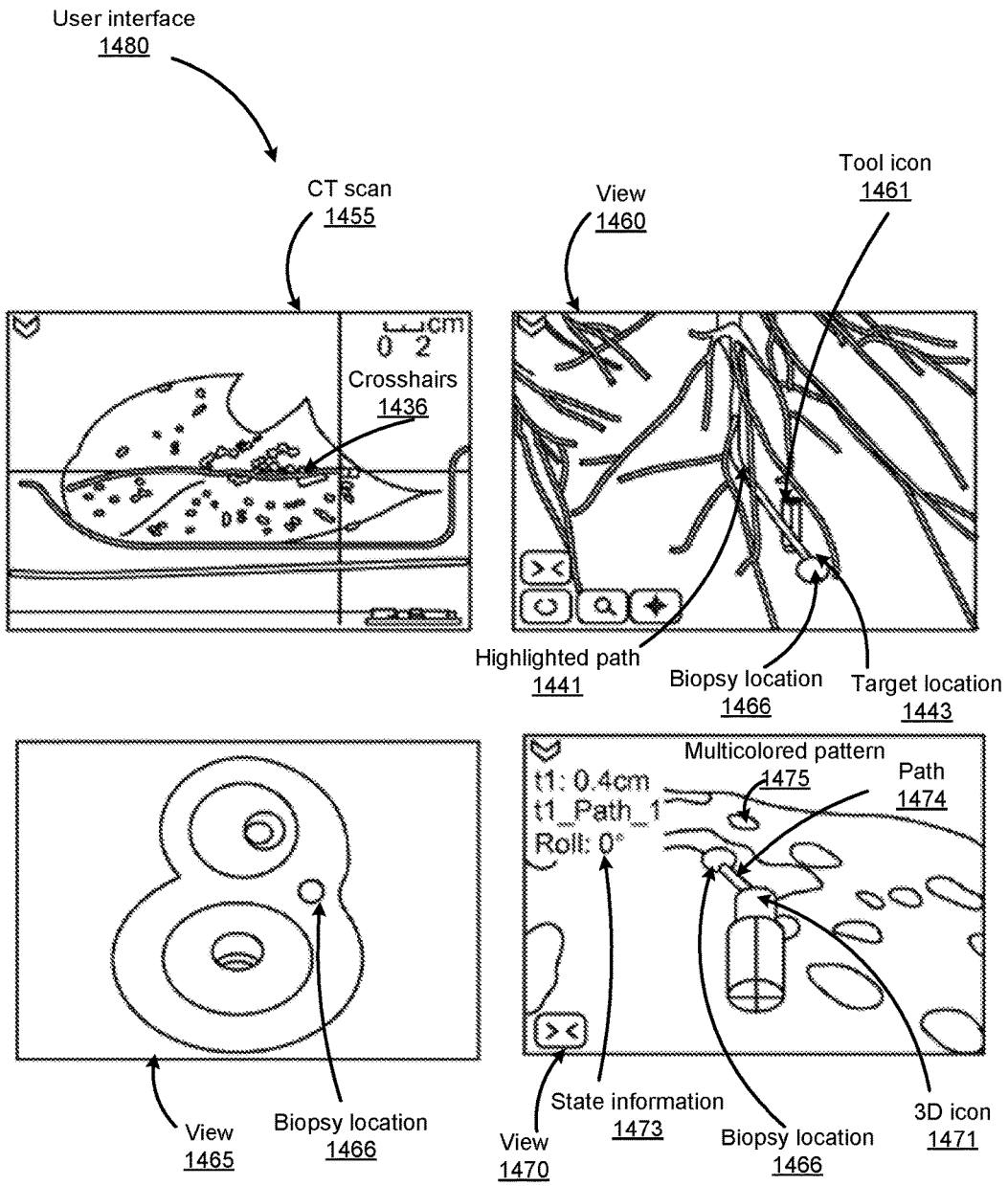
FIG. 14C shows an example user interface for tool alignment and control during an endoscopic procedure, according to one embodiment.

Navigating to a particular point in a tubular network of a patient's body requires certain steps to be taken pre-operatively in order to generate the information needed to create the 3D model of the tubular network and to determine a navigation path within it. FIGS. 14A-14C show example pre-operative steps for preparation of a surgical instrument (e.g., an instrument tip) to navigation through an example tubular network, according to various embodiments.

FIG. 14A shows an example pre-operative sequence of steps of a method 1400 for navigating the instrument tip to a particular site within the tubular network, according to one embodiment. Alongside each step of the method 1400, a corresponding image is shown to illustrate a representation of the involved data for planning a path and navigating through the tubular network.

Initially, in step 1405, a CT scan of the tubular network is obtained, and the data from the CT scan provides 3D information about the structure and connectivity of the tubular network. For example, the image in step 1405 shows a tomographic slice of a patient's lungs.

In step 1410, a 3D model is generated based on the obtained CT scan data, and the generated 3D model can be used to assign each branch of the tubular network with a unique identity, enabling convenient navigation within the network. For example, the image in step 1410 shows a 3D model of a patient's bronchial network.

In step 1415, a target 1416 is selected, and this target may be, for example, a lesion to biopsy, or a portion of organ tissue to repair surgically. In one embodiment, the user is capable of selecting the location of the target by interfacing with a computer display that can show the 3D model, such as by clicking with a mouse or touching a touchscreen. The selected target may then be displayed to the user. For example, the target 1416 is marked within the 3D bronchial model generated from step 1410.

In step 1420, a path 1421 is automatically planned from an entry point 1422 to the target 1416, and the path 1421 identifies a sequence of branches within the network to travel through, so as to reach the target 1416. In one embodiment, the tubular network may be tree-like, the path 1421 may be uniquely determined by the structure of the tubular network, while in another embodiment, the tubular network may be cyclic, and the path may be found by an appropriate algorithm such as a shortest-path algorithm.

Once the path 1421 has been determined, virtual endoscopy 1425 may be performed to give the user a preview of the endoscopic procedure. The 3D model generated from step 1410 is used to generate a sequence of 2D images as though seen by an endoscope tip while navigating the network corresponding to the 3D model. The path 1421 may be shown as a curve that may be followed to get from the entry point 1422 to the target 1416.

Once the virtual endoscope tip has arrived at the target 1416, a virtual tool alignment procedure 1430 may be performed to illustrate to the user how to manipulate endoscopic tools in order to perform a surgical procedure at the target. For example, in the illustration, a virtual endoscopic biopsy needle 1431 is maneuvered by the user in order to biopsy a lesion 1432 located beneath the surface of a bronchial tube. The lesion location is highlighted so that the user can align the needle to it, and then use the needle to pierce the surface of the bronchial tube and access the lesion underneath. This mimics the steps that will be taken during the actual surgical procedure, allowing the user to practice before performing surgery.

FIG. 14B shows an example user interface 1434 for navigation of a surgical instrument through a tubular network, according to one embodiment. The user interface 1434 allows the user to have various views of the tubular network during an endoscopic procedure. In addition to a real-time view from the imaging device (e.g., an endoscope camera), the user interface 1434 may show various navigation views to the user. For example, the location of the endoscope tip may be superimposed on a tomographic segment of the CT scan 1435, with a marker (e.g., crosshairs 1436) showing the location of the instrument. In this case, the CT image is of a patient's lungs, and the endoscope used is a bronchoscope.

In FIG. 14B, the user interface 1434 also shows a view 1440 representing a 3D model with a highlighted path 1441 and icons showing the endoscope location 1442 and the target location 1443. Some additional icons 1444 are also shown in the view 1440 for user interface controls enabling features as map pan and zoom.

View 1445 shows a virtual endoscope view from the estimated location of the tip that can be compared with a real-time view to confirm that the tip location has been estimated accurately. A path indicator 1446 and location/orientation indicator 1447 for aid in navigation is also shown in the view 1446. The upper left shows state information 1448 determined by the state estimator 980, indicating that the current distance to target "t1" is 5.4 cm, and that the calculated roll angle is −139 degrees.

View 1450 shows a virtual view of the endoscope shaft 1451, displayed from a "third-person" viewpoint to the rear of the endoscope tip. The virtual view can be generated by assuming that the endoscope shaft lies along the path already traversed by the tip, and the view of the surrounding area is generated based on the 3D model in the vicinity of the chosen viewpoint. Alternately, the view may be generated from images taken while passing through that area earlier in the procedure. In alternative embodiments, the virtual viewpoint may project ahead of the endoscope tip location, to show the next bifurcation. This view may further highlight the intended path, to inform the user in advance which way to steer when the endoscope tip reaches the next bifurcation.

FIG. 14C shows an example user interface 1480 for tool alignment and control during an endoscopic procedure, according to one embodiment. View 1455 shows a tomographic view at a later stage in the procedure than view 1435, in which the endoscope tip is near the target and an endoscopic tool—in this case, a biopsy needle—has been deployed from the endoscope's working channel. The crosshairs 1436 highlights the new position of the tip. Since the bronchoscope in the image is farther into the patient's lungs, the tomographic slice has changed to show a deeper cross-sectional segment. The icon locating the endoscope tip has been replaced with one indicating the location and orientation of the needle. View 1460 shows a map view of the 3D model, zoomed in around the target location 1443 and the tool icon 1461 representing the biopsy needle. Located at target 1443 is a biopsy location 1466 to which a biopsy needle is to be applied. As shown in this view, the endoscope tip has been navigated to nearly the end of path 1441, to arrive at a location close enough to the target location 1443 so that the needle may reach the biopsy location 1466.

View 1465 shows a virtual view in the vicinity of target location 1443, highlighting a biopsy location 1466 to help the user visualize precisely where the needle is to be inserted to collect tissue for biopsy. Additional information, such as target size and distance to target may optionally be overlaid on the image.

View 1670 shows a close-up view of a 3D icon 1471 representing a biopsy needle, superimposed on a tomographic image of the patient's lungs. The roll of the instrument is indicated by a multicolored pattern 1475 on the rear of the 3D icon 1471. As seen from state information 1473, this particular orientation represents a roll of 0 degrees, and the needle is currently 4 mm from the biopsy location 1466. A path 1474 is displayed showing how the needle should be oriented and moved in order to contact the biopsy location 1466.

VIII. Machine Configuration for the Navigation Configuration System

More generally, the navigation and tracking technique disclosed herein may be performed with an appropriately configured computer system. A processor within the computer system may comprise one or more components to process electronic signals, and may comprise one or more of a central processor unit, a video processor, logic circuitry, gate array logic, filed programmable gate array, integrated circuit, or application specific integrated circuit. The computer system includes a central processing unit (CPU, also "processor" and "computer processor" herein), which can be a single core or multi core processor, or a plurality of processors for parallel processing. The CPU can execute a sequence of machine-readable instructions, which can be embodied in a program or software. The instructions may be stored in a memory location. Examples of operations performed by the CPU can include fetch, decode, execute, and writeback. The CPU can be part of a circuit, such as an integrated circuit. One or more other components of the system can be included in the circuit. In some cases, the circuit comprises an application specific integrated circuit (ASIC).

The computer system may also include one or more of memory or memory locations (e.g., random-access memory, read-only memory, flash memory), electronic storage units (e.g., hard disk), communication interfaces (e.g., network adapters) for communicating with one or more other systems, and peripheral devices, such as caches, other memory, data storage and/or electronic display adapters. The memory, storage unit, interface, and peripheral devices are in communication with the CPU through a communication bus, such as a motherboard.

The storage unit can be a data storage unit (or data repository) for storing data. The computer system can be operatively coupled to a computer network ("network") with the aid of the communication interface. The network can be the Internet, an interne and/or extranet, or an intranet and/or extranet that is in communication with the Internet. The network in some cases is a telecommunication and/or data network, and can include can include one or more computer servers. The storage unit can store files, such as drivers, libraries and saved programs. The storage unit can store user data, e.g., user preferences and user programs. The computer system in some cases can include one or more additional data storage units that are external to the computer system, such as located on a remote server that is in communication with the computer system through an intranet or the Internet.

Methods as described herein can be implemented by way of machine (e.g., computer processor) executable code stored on an electronic storage location of the computer system, such as, for example, on the memory or electronic storage unit. The machine executable or machine readable code can be provided in the form of software. During use, the code can be executed by the processor. In some cases, the code can be retrieved from the storage unit and stored on the memory for ready access by the processor. In some situations, the electronic storage unit can be precluded, and machine-executable instructions are stored on memory.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Methods and systems of the present disclosure can be implemented by way of one or more methods. A method can be implemented with a processor as described herein, for example by way of software upon execution by one or more computer processors.

IX. Additional Considerations

Alternative views and embodiments of the surgical robotics system 1100, the surgical robotics system 1200, and other surgical robotics systems including the above mentioned components are further illustrated and described at least in U.S. Provisional Application No. 62/162,486 filed May 15, 2015, U.S. Provisional Application No. 62/162,467 filed May 15, 2015, U.S. Provisional Application No. 62/193,604 filed Jul. 17, 2015, U.S. Provisional Application No. 62/201,518 filed Aug. 5, 2015, U.S. Provisional Application No. 62/203,530 filed Aug. 11, 2015, and U.S. Provisional Application No. 62/235,394 filed Sep. 30, 2015.

Upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context unless otherwise explicitly stated.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

What is claimed is:

1. A system comprising:
   a set of one or more processors; and
   a computer readable-medium that includes computer program instructions that, when executed, cause the set of processors to:
      access a first set of sensor data regarding physical manipulation of an elongated medical instrument inserted into a tubular network of a patient, the first set of sensor data being derived from at least a first set of one or more sensors located at a proximal portion of the of the elongated medical instrument;
      access a second set of sensor data regarding the positioning of the medical elongated medical instrument, the second set of sensor data being derived from at least a second set of one or more sensors located within the elongated medical instrument, the second set of sensors being different from the first set of sensors;
      determine a first estimated state regarding the physical manipulation of the elongated medical instrument based on the first set of sensor data;
      determine a second estimate state regarding the physical manipulation of the elongated medical instrument based on the second set of sensor data; and
      determine an estimated state of the elongated medical instrument based on the first estimated state and the second estimated state.

2. The system of claim 1 wherein instructions, when executed, cause the set of one or more processors to access a third set of sensor data regarding the positioning of the medical elongated medical instrument, the third set of sensor data being derived from at least a third set of one or more sensors, the third set of sensors being different from the first and second set of sensors.

3. The system of claim 2, wherein the instructions, when executed, cause the set of one or more processors to determine a third estimate state regarding the elongated medical instrument based on the third set of sensor data.

4. The system of claim 1, wherein the instructions, when executed, cause the set of one or more processors to associate the first estimated state with a first confidence value, to associate the second estimated state with a second confidence value, and to determine the estimated state of the elongated medical instrument based on the first estimated state, the second estimated state, the first confidence value and the second confidence value.

5. The system of claim 4, wherein the confidence value for a corresponding one of the estimated states represents a degree of confidence in the determination of the corresponding estimated state.

6. The system of claim 1, wherein accessing the first set of sensor data regarding physical manipulation of the elongated medical instrument inserted into a tubular network of a patient comprises accessing robotic data regarding the physical manipulation of an elongated medical instrument inserted into a tubular network of a patient.

7. The system of claim 6, wherein the robotic data includes at least one of: pitch, roll, and yaw of a tip of the instrument, the pitch, the roll, and the yaw based on retraction of at least one of a plurality of cables of the elongated medical instrument and insertion distance of the elongated medical instrument into the tubular network.

8. The system of claim 1, wherein accessing the first set of sensor data regarding physical manipulation of the elongated medical instrument inserted into a tubular network of a patient comprises accessing image data captured by an imaging device located proximal to an instrument tip of the elongated medical instrument.

9. The system of claim 8, wherein the image data is based on a series of images captured sequentially in time.

10. The system of claim 1, wherein accessing the second set of sensor data regarding the positioning of the medical elongated medical instrument comprises accessing electromagnetic (EM) data captured using an EM sensor located proximal to a tip of the medical elongated medical instrument and using at least on external EM sensor or EM generated located external to the patient.

11. The system of claim 1, wherein the elongated medical instrument is a flexible endoscope comprising an endolumenal structure and a plurality of cables that are configured to change a direction of a tip of the instrument.

12. The system of claim 1, wherein the estimated state indicates location of the instrument tip within the tubular network.

13. The system of claim 1, wherein the instructions, when executed, cause the set of one or more processors to access a prior estimated state for medical elongated medical instrument based on data captured at a prior instant in time and determe at least one of the first and second estimated states based on the prior estimated state.

14. The system of claim 1, wherein determining the second estimated state further comprises performing registration of an EM system to a 3D model, the EM system including coordinates based on received EM data and the 3D model including coordinates based on a 3D model of the tubular network; and the second estimated state based on the performed registration.

15. The system of claim 1, wherein the 3D model of the tubular network is generated based on computerized axial tomography (CT) scans of the tubular network.

16. The system of claim 1, wherein determining second estimated state further comprises: determining an estimate of position and orientation of the instrument tip relative to possible branches within the tubular network.

17. The system of claim 1, wherein the second estimated state is represented as a discrete probability distribution, each of values of the probability distribution indicating a likelihood of a tip of an instrument being inside a corresponding branch among the possible branches.

18. The system of claim 1, wherein determining the first estimated state further comprises: measuring movement of the elongated medical instrument within the tubular network based on accessed image data; and generating the first estimated state based on the measured movement.

19. A non-transitory computer readable storage medium comprising computer program instructions that when executed by a set of one or more processors cause the set of processors to:
  access first set of data from a first set of one or more sensors regarding physical manipulation of an elongated medical instrument inserted into a tubular network of a patient;
  access second set data captured by as second set of one or more sensors located proximal to an instrument tip of the elongated medical instrument;
  determine a first estimated state for the instrument tip based on the first set of data;
  determine a second estimated state for the instrument tip based on the second set of data; and
  determine an estimated state for the instrument tip based on the first and second estimated states.

20. The non-transitory computer readable storage medium of claim 19 wherein the instructions, when executed, cause the at least one processor to access a third set of data captured using a third set of sensors comprising one more sensors located proximal to an instrument tip of the elongated medical instrument.

21. The non-transitory computer readable storage medium of claim 20 wherein the instructions, when executed, cause the at least one processor to determine a third estimated state for the instrument tip based on the third set of data.

22. The non-transitory computer readable storage medium of claim 21 wherein the instructions, when executed, cause the at least one processor to determine the estimated state for the instrument tip based on the first, second and third estimated states.

23. The non-transitory computer readable storage medium of claim 19 wherein the instructions, when executed, cause the at least one processor when accessing first set of data to access robotic data regarding the physical manipulation of an elongated medical instrument inserted into a tubular network of a patient.

24. The non-transitory computer readable storage medium of claim 23 wherein the robotic data includes at least one of: pitch, roll, and yaw of a tip of the instrument, the pitch, the roll, and the yaw based on retraction of at least one of a plurality of cables of the elongated medical instrument and insertion distance of the elongated medical instrument into the tubular network.

25. The non-transitory computer readable storage medium of claim 19 wherein the instructions, when executed, cause the at least one processor when accessing the first set of sensor data to access image data captured by an imaging device located proximal to an instrument tip of the elongated medical instrument.

26. The non-transitory computer readable storage medium of claim 25 wherein the image data is based on a series of images captured sequentially in time.

27. The non-transitory computer readable storage medium of claim 19 wherein the instructions, when executed, cause the at least one processor when accessing the second set of sensor data to access electromagnetic (EM) data captured using an EM sensor located proximal to a tip of the medical elongated medical instrument and using at least on external EM sensor or EM generated located external to the patient.

28. The non-transitory computer readable storage medium of claim 19 wherein the estimated state indicates location of the instrument tip within a tubular network.

29. The non-transitory computer readable storage medium of claim 19 wherein the instructions, when executed, cause the at least one processor to associate the first estimated state with a first confidence value and to associate the second estimated state with a second confidence value.

30. The non-transitory computer readable storage medium of claim 29 wherein the instructions, when executed, cause the at least one processor to determine an estimated state for the instrument tip based on the first and second estimated states and the first and second confidence values.

* * * * *